US006994849B2

(12) United States Patent
Droby

(10) Patent No.: US 6,994,849 B2
(45) Date of Patent: Feb. 7, 2006

(54) **YEAST *METSCHNIKOWIA FRUCTICOLA* NRRL Y-30752 FOR INHIBITING DELETERIOUS MICROORGANISMS ON PLANTS**

(75) Inventor: Samir Droby, Baqa El-Gerberia (IL)

(73) Assignee: State of Israel, Ministry of Agriculture, Agricultural Research Organization, Beit Dagan (IL)

( * ) Notice: Subject to any disclaimer, the term of this patent is extended or adjusted under 35 U.S.C. 154(b) by 0 days.

(21) Appl. No.: 10/471,827

(22) PCT Filed: Mar. 13, 2002

(86) PCT No.: PCT/US02/07525

§ 371 (c)(1),
(2), (4) Date: Feb. 9, 2004

(87) PCT Pub. No.: WO02/072777

PCT Pub. Date: Sep. 19, 2002

(65) Prior Publication Data

US 2004/0115171 A1    Jun. 17, 2004

Related U.S. Application Data

(60) Provisional application No. 60/275,526, filed on Mar. 14, 2001.

(51) Int. Cl.
*A01N 25/00* (2006.01)
*A01N 25/32* (2006.01)
*A01N 63/00* (2006.01)
*C12N 1/00* (2006.01)
*C12N 1/20* (2006.01)

(52) U.S. Cl. ............... 424/93.51; 424/405; 424/406; 435/255.1; 435/911

(58) Field of Classification Search ............ 435/257.1, 435/243, 255.1, 911; 424/405, 93.1, 406, 424/93.51
See application file for complete search history.

(56) References Cited

U.S. PATENT DOCUMENTS 6,022,698 A  *  2/2000  Chen et al. .................. 435/24
6,287,779 B1 *  9/2001  Engel et al. .................. 435/6

* cited by examiner

*Primary Examiner*—David M. Naff
*Assistant Examiner*—Deborah K. Ware
(74) *Attorney, Agent, or Firm*—Browdy and Neimark, PLLC

(57) ABSTRACT

A biologically pure culture of a yeast of the species *Metschnikowia fructicola*. The yeast is identified as NRRL Y-30752 and is capable of inhibiting growth of a deleterious micro-organism on a portion of a plant to which a biologically effective amount of a culture of the yeast is applied. Further disclosed is a composition for use in protection of agricultural produce including a biologically effective amount of *Metschnikowia fructicola* and a carrier. Further disclosed is an article of manufacture including packaging material and the disclosed composition which is identified for use in protection of agricultural produce from a deleterious micro-organism. Further disclosed is a method of inhibiting growth of a deleterious micro-organism on a portion of a plant including applying at least one time an agriculturally effective amount of yeast of the genus *Metschnikowia* to the portion of a plant.

17 Claims, 16 Drawing Sheets grape wine / field
(-1) = 1/10 dilution

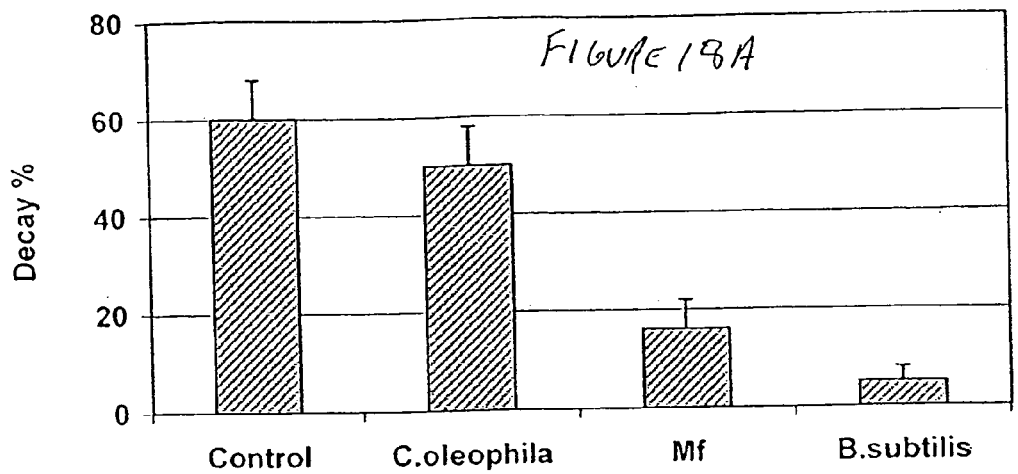
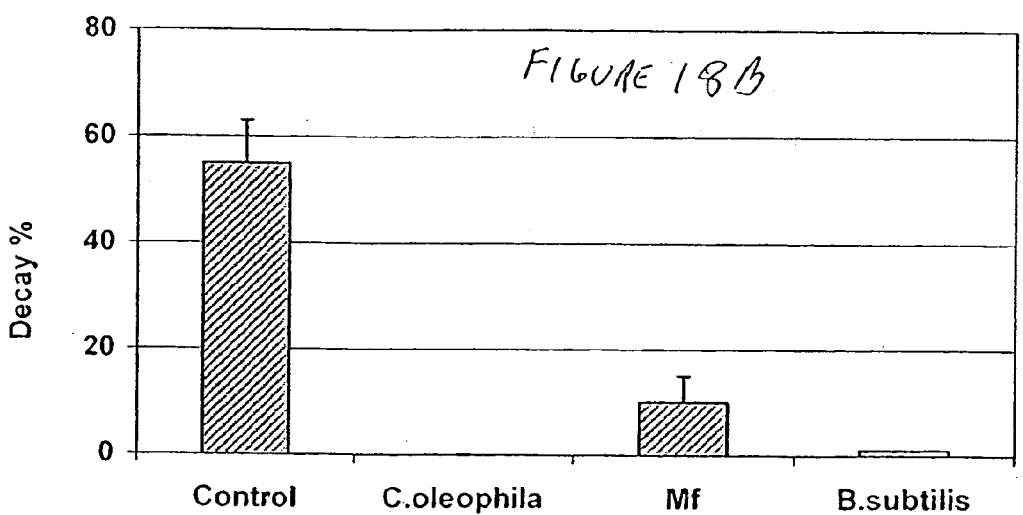
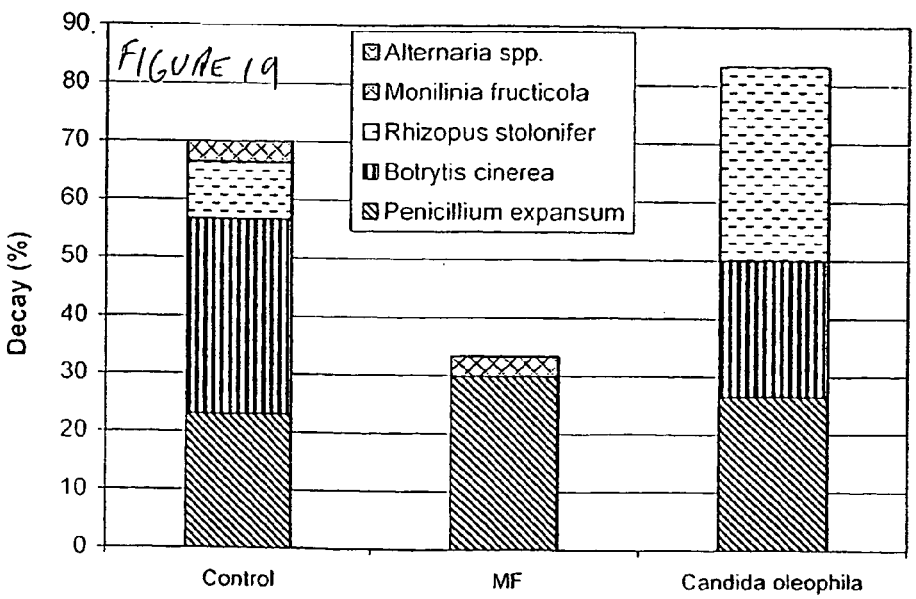

YEAST *METSCHNIKOWIA FRUCTICOLA* NRRL Y-30752 FOR INHIBITING DELETERIOUS MICROORGANISMS ON PLANTS

This application claims priority PCT/US02/07525 filed on Mar. 13, 2002 and from U.S. Patent Application 60/275,526 filed on Mar. 14, 2001 and now abandoned.

FIELD AND BACKGROUND OF THE INVENTION

The present invention relates to a novel antagonistic yeast useful in controlling spoilage of agricultural produce, methods of use thereof and compositions containing same. Specifically, the present invention relates to the yeast *Metschnikowia fructicola* and to use thereof to inhibit growth of unwanted microorganisms on a portion of a plant, for example, foliage, flowers, fruit, roots or vegetables.

One of the most serious problems in the modern produce (fruit, vegetable and flower) industry is decay or spoilage of produce after harvest. It is estimated that postharvest losses of fruits and vegetables are 50%. This loss is attributable to fungal and bacterial infections to a great degree. In developing countries, postharvest losses are often severe due to the lack of adequate handling and refrigerated storage facilities. While developed nations have adequate refrigeration, consumers in these countries often purchase produce which has been shipped great distances and stored for prolonged periods of time. Postharvest decay of fruits and vegetables can be traced to infections that occur either between flowering and fruit maturity or during harvesting and subsequent handling and storage.

Synthetic fungicides such as imazalil and thiabendazole (TBZ) have traditionally been a primary means of controlling postharvest produce loss. However, there is increasing global pressure to reduce the use of toxic chemicals in the food industry. Consumers are concerned about chemical residues on fruit and vegetables in general and are especially uncomfortable with the idea of postharvest application of chemicals.

In addition, environmentalists are becoming increasingly vocal about chemical pesticide disposal and levels of chemical residues on fresh produce.

Concurrently, fungicide-resistant strains of pathogens have emerged to most commonly used fungicides (e.g. TBZ, Imazalil, Rovral). Finally, some of the more effective fungicides such as Captan and Benlate have been deregistered and are no longer available. Further, postharvest treatment of some types of produce is not permitted. In addition, much postharvest spoilage is the result of pathogens which colonized produce prior to harvest.

All of these factors have contributed to increased interest in the development of effective alternatives which pose no risk to human health and the environment. Use of biological approaches such as natural compounds, induced resistance and antagonistic microorganisms in plants have all been proposed as potential alternatives to synthetic fungicides for prevention or control of decay of agricultural produce.

Natural compounds are typically expensive to produce and of limited efficacy. Of the biological approaches, they hold the least promise.

Induced resistance holds considerable promise in theory but has suffered from two problems in other instances where it has been tried. Induced resistance based on genetically modified organisms (GMOs) has often had disappointing results because pathogens mutate when the GMOs are widely deployed in the field. However, the more complicated problem with GMOs has proven to be resistance to GMOs in general by consumers and environmentalists.

This leaves development of antagonistic microorganisms as the remaining "acceptable" biological approach.

In recent years, research on the use of microbial biocontrol agents for the control of postharvest diseases of fruits has gained considerable attention and has moved from the laboratory to commercial application. From these efforts, a large body of information regarding the use of microbial biocontrol agent to control postharvest diseases is now available (Droby et al., 2001). The selection of putative microbial antagonists has been based mainly on the ability of antagonists to rapidly colonize fruit surfaces and wounds, out compete the pathogen for nutrients, and survive and develop under a wide range of temperature conditions. Antagonists which can be used in the presence of agricultural chemicals, including antibiotics, have not been previously characterized.

A simple and reliable screening technique for selecting antagonists has been developed utilizing the wound site as a selective medium. Utilizing these procedures and other comparable protocols, several antagonistic bacteria, yeasts, and filamentous fungi have been isolated and shown to protect a variety of harvested commodities including citrus and pome fruit against postharvest decay (Droby et al., 1989; Janisiewicz and Roitman, 1988; Chalutz and Wilson, 1990; Roberts, 1990; Droby et al., 1991; Gullino et al., 1991; Janisiewicz, 1994; Lurie et al., 1995; Chand-Goyal and Spotts, 1996; El Ghaouth et al., 1998; Ippolito et al., 2000).

The success of some of these microbial antagonists in laboratory and large scale studies has generated interest by several agro-chemical companies in the development and promotion of postharvest biological products for control rots of fruits and vegetables. A number of microbial antagonists have been patented and evaluated for commercial use in postharvest treatment of produce. Currently, four antagonistic microorganisms, two yeasts, *Candida oleophila*, and *Cryptococcus albidus* and two strains of a bacterium, *Pseudomonas syringae* are commercially available under the trade names ASPIRE, YieldPlus, and BIOSAVE-110 and BIOSAVE-111 respectively.

Patents describing use of bacteria and yeasts for biological control of fungal diseases of agricultural commodities include U.S. Pat. No. 5,314,691 (Coffey et al.); U.S. Pat. No. 5,270,059 (Janisiwicz et al.); U.S. Pat. No. 5,266,316 (Elad et al.); U.S. Pat. No. 5,244,680 (Roberts); U.S. Pat. No. 5,238,690 (Elad et al.); U.S. Pat. No. 5,041,384 (Wilson and Chalutz); U.S. Pat. No. 5,711,946 (Goyal and Roberts) and PCT publications WO 92/18009 (Shanmuganathan) and WO 91/01641 (Wilson et al.). Each of these prior art teachings is narrowly defined as a composition or method containing/employing a disclosed species or strain of bacteria, fungus or yeast. None of these teachings includes a micro-organism which has proved effective against a wide range of fungal pathogens in a wide range of agricultural commodities. Further, none of these patents contain a hint or a suggestion that yeast of the genus *Metschnikowia* are useful in preventing post harvest loss of produce.

*Metschnikowia pulcherrima* is known to have some efficacy in biological control of a few deleterious microorganisms on fruit (DeCurtis et al. (1996) Ann. Microbiol. Enzymol. 46: 45–55 and Piano et al. (1997) Postharvest Biol. Technol. 11:131–140), however it is a separate and distinct species from *Metschnikowia fructicola*. Further, the apparently limited spectrum of antagonist activity of *Metschnikowia pulcherrima* renders it ill suited for use in the produce industry. Thus far, only a limited spectrum of biocontrol activity for *M. pulcherrima* has been demonstrated. This renders it ill suited to commercial prevention pre- and postharvest in a wide variety of agricultural settings.

There is thus a widely recognized need for, and it would be highly advantageous to have, a novel antagonistic yeast useful in controlling spoilage of agricultural produce, methods of use thereof and compositions containing same devoid of the above limitations.

SUMMARY OF THE INVENTION

According to one aspect of the present invention there is provided A biologically pure culture of a yeast of the species *Metschnikowia fructicola* identified as NRRL Y-30752, the culture capable of competitively inhibiting growth of a deleterious micro-organism on a fruit to which a biologically effective amount of the culture is applied. *Metschnikowia fructicola* (MF), is referred to herein as strain #277 and has been deposited in the NRS culture collection (NRRL) National Center for Agricultural Utilization Research, Peoria, Ill., USA where it has been assigned deposit number NRRL Y-30752. This deposit has been made in compliance with the terms of the Budapest Treaty.

According to another aspect of the present invention there is provided a composition for use in protection of agricultural produce includes, as an active ingredient, a biologically effective amount of yeast of biologically pure *Metschnikowia fructicola* the composition further containing a carrier.

According to yet another aspect of the present invention there is provided a method of inhibiting growth of a deleterious micro-organism on a portion of a plant, the method includes applying at least one time an agriculturally effective amount of biologically pure culture of a yeast of the genus *Metschnikowia* to the portion of a plant. Application may be pre-harvest, concurrent with harvest or post-harvest.

According to still another aspect of the present invention there is provided an article of manufacture includes packaging material and a composition identified for use in protection of agricultural produce from a deleterious micro-organism includes, as an active ingredient, a biologically effective amount of yeast of biologically pure *Metschnikowia fructicola* the composition further containing a carrier.

According to further features in preferred embodiments of the invention described below, there is provided a biologically pure strain of *Metschnikowia fructicola* having all of the identifying characteristics of the biologically pure culture of NRRL Y-30752.

According to still further features in the described preferred embodiments there is provided a biologically pure mutant of *Metschnikowia fructicola*, having all of the identifying characteristics of the biologically pure culture of NRRL Y-30752.

According to still further features in the described preferred embodiments the deleterious micro-organism is selected from the group consisting of *Botrytis cinerea, Aspergillus niger, Penicillium digitatum, Penicillium expansum, Rhizopus stolonifer Alternaria* spp., *Molinilia* spp. and *Fusarium* spp.

According to still further features in the described preferred embodiments the portion of a plant is selected from the group consisting of a stone fruit, a pome fruit, a citrus fruit, grapes, a vegetable, a flower bulb, an herb, a grain, a root, a leaf, a grain and berries.

According to still further features in the described preferred embodiments the yeast is supplied in a physiologic state selected from the group consisting of active and dormant.

According to still further features in the described preferred embodiments the yeast is supplied in a physical form selected from a liquid suspension, an emulsion, a powder, granules, a lyophylsate and a gel.

According to still further features in the described preferred embodiments the composition further includes a chemical antibiotic.

According to still further features in the described preferred embodiments the chemical antibiotic is a fungicide or an antimicrobial agent or a pesticide.

According to still further features in the described preferred embodiments the fungicide includes at least one chemical selected from the group consisting of Iprodione, Thiabendazole, Imazalil (1-(2-2,4-Dichlorophenyl)-2(2-propenyloxy-ethyl)-1Himidazol), Fenhexamide, Pyrimethamil and a combination of Fludioxonyl and Cyprodinil (e.g. Rovral, TBZ, Imazalil, Teldor, Mitos or Switch).

According to still further features in the described preferred embodiments the yeast of the genus *Metschnikowia* has all of the identifying characteristics of the species *Metschnikowia fructicola* identified as NRRL Y-30752 or of any strain thereof or of any mutant of such a strain.

According to still further features in the described preferred embodiments article of manufacture further includes an applicator designed and constructed to apply the yeast to the agricultural produce.

The present invention successfully addresses the shortcomings of the presently known configurations by providing a novel antagonistic yeast of the genus *Metschnikowia* useful in controlling spoilage of many types agricultural produce caused by a broad spectrum of micro-organisms. The present invention further provides methods of use of the yeast, compositions containing the yeast and articles of manufacture containing the compositions. The present invention is expected to enjoy wide acceptance because it can provide post-harvest production from a pre-harvest application.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIGS. 18A and B are histograms illustrating efficacy of the yeast *Metschnikowia fructicola* (Mf) of the present invention, as compared to *C. oleophila* and *B. subtilis* in controlling *Penicillium hirsutum* rot on Easter Lilly bulbs.

FIG. 19 is a histogram illustrating total percent decay from natural infection of nectarines with various pathogens during storage at 0 C for 30 days and additional 10 days of room temperature storage in the presence of *Metschnikowia fructicola* (Mf) of the present invention or *Candida oleophila*.

DESCRIPTION OF THE PREFERRED EMBODIMENTS

Figure 1:
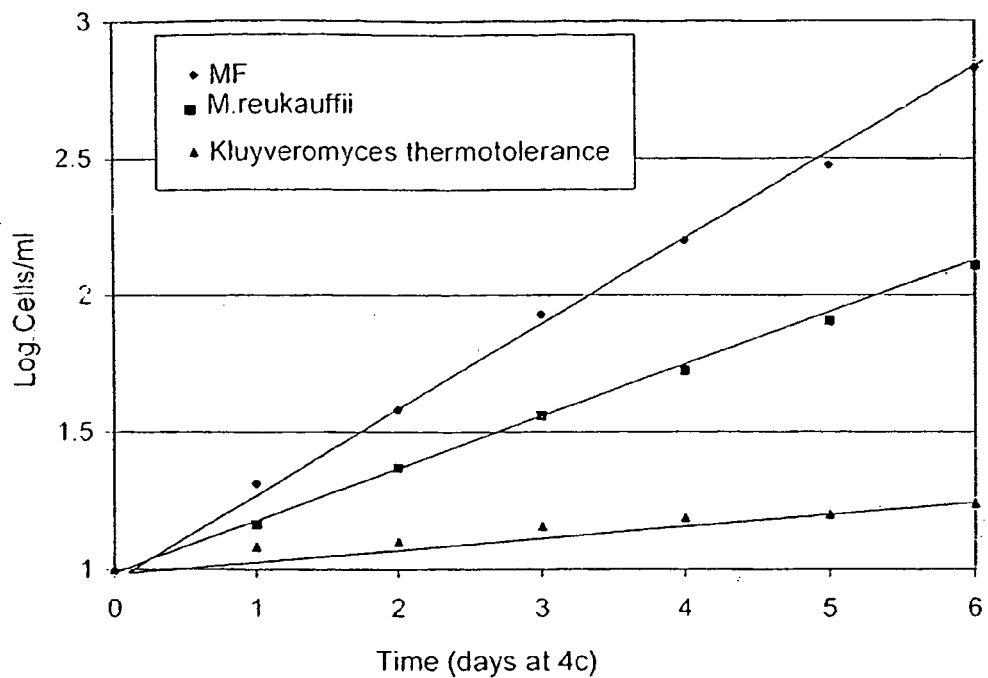
FIG. 1 is a graph of cell number as a function of time for the yeasts *Metschnikowia fructicola* (Mf) of the present invention and *Metshnikowia reukafii* (231) and *kluyveromyces thermotolerance* (414) incubated at 4° C. indicating that Mf grows faster than other yeasts in the cold.

The present invention is of a new yeast species *Metschnikowia fructicola* which can be applied to agricultural produce to reduce pre-harvest and postharvest decay via competitive inhibition of a wide range of micro-organisms. *Metschnikowia fructicola* is referred to herein as strain #277 and/or Mf and has been deposited in the NRS culture collection (NRRL) National Center for Agricultural Utilization Research, Peoria, Ill., USA where it has been assigned deposit number NRRL Y-30752. This deposit has been made in compliance with the terms of the Budapest Treaty.

Specifically, the present invention can be used to reduce the incidence and/or severity of fungal pathogens of grapes, citrus fruit, pome fruit, stone fruit, strawberries, flower bulbs, vegetables, roots, grains, foliage and herbs.

"Grapes", as used in this specification and the accompanying claims, includes table grapes and wine grapes.

"Citrus fruit", as used in this specification and the accompanying claims, includes, but is not limited to, oranges, grapefruit, tangerines, clementines, lemons, limes, kumqwat, citroen, pomello, mandarin and hydrids derived therefrom.

"Pome fruit", as used in this specification and the accompanying claims, includes, but is not limited to, apples, pears and quinces.

"Stone fruit", as used in this specification and the accompanying claims, includes, but is not limited to, peaches, plums, nectarines, apricots, mangos.

For purposes of this specification and the accompanying claims the terms "inhibiting" and "inhibition" refer to retardation or delay of a process. As such, inhibition may be deemed to occur if the process occurs at a reduced rate as a result of application of a claimed yeast, a composition containing such a yeast, or as a result of practice of a claimed method.

The invention is further of methods of use of the claimed yeast, compositions containing the claimed yeast and articles of manufacture including those compositions.

The principles and operation of protection of agricultural produce against unwanted decay via competitive inhibition according to the present invention may be better understood with reference to the figures and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided A biologically pure culture of a yeast of the species *Metschnikowia fructicola* identified as NRRL Y-30752. This culture is capable of competitively inhibiting growth of a wide range of deleterious micro-organisms on a portion of a plant to which a biologically effective amount of the culture is applied. Identifying characteristics of *Metschnikowia fructicola* are set forth in "*Metschnikowia fructicola*, a New Ascoropic Yeast with Potential for Biocontrol of Postharvest Fruit Rots" (Kurtzman and Droby (2001) System Appl. Microbiol 24: in press) which is fully incorporated herein by reference. Briefly, NRRL Y-30752 differs from other members of the genus *Metschnikowia* in the D1/D2 domain of the 26S rDNA sequence. Specifically, NRRL Y-30752 differs by 2.2% from *Metschnikowia pulcheirma*, which is its closest known relative. It is well accepted that differences of 1% are sufficient for differentiation between species (Kurtzman and Robnett (1998) Antonie Leeuwenhoek 73:331–371). Therefore, *Metschnikowia* which differ from Mf by less than 1% in the D1/D2 domain of the 26S rDNA sequence are deemed to be within the scope of the present invention.

Thus, any biologically pure strain of *Metschnikowia fructicola*, whether physically derived from the original deposit or independently isolated, is part of the present invention so long as it possesses all of the identifying characteristics of NRRL Y-30752. This includes biologically pure mutants of *Metschnikowia fructicola*, so long as they retain all of the identifying characteristics of NRRL Y-30752. For purposes of this specification and the accompanying claims, the term "mutant" includes both naturally occurring mutations and purposeful genetic modifications such as introduction of point mutations, plasmids, phages, phagemids, cosmids and artificial chromosomes.

The deleterious micro-organism which Mf protects against include, but are not limited to, *Botrytis cinerea, Aspergillus niger, Penicillium digitatum, Penicilium italicum, Penicillium expansum, Geotrichum candidum, Rhizopus stolonifer, Alternaria* spp., *Molinilia* spp, and *Fusarium* spp.

The present invention is further embodied by a composition for use in protection of agricultural produce. The composition includes, as an active ingredient, a biologically effective amount of yeast of biologically pure *Metschnikowia fructicola*. The composition further contains a carrier. As illustrated in examples set forth hereinbelow, *Metschnikowia fructicola* is biologically effective when delivered at a concentration in excess of $10^6$ cells/ml, preferably in excess of $10^7$ cells/ml, more preferably $10^8$ cells/ml, most preferably $10^9$ cells/ml or more.

The yeast of the composition may be supplied in any physiologic state such as active or dormant. Dormant yeast may be supplied, for example, frozen (e.g in DMSO/glycerol), dried or lyophilized. Further, the yeast of the composition may be supplied in any physical form including, but not limited to a liquid suspension, an emulsion, a powder, granules, a lyophylisate or a gel.

The composition may be applied as spray or drench or as an aerosolized powder or ointment. If the composition includes dormant yeast, they may require re-activation prior to use, for example by rehydration and or incubation in a nutrient medium. Preferably, dormant yeast will become active when applied or subsequent to application.

In order to increase the overall efficacy of the composition, a chemical antibiotic may be further included. Preferably, the chemical antibiotic is a compatible fungicide, for example Iprodione (e.g. Rovral) or Thiabendazole (e.g. Apl-Luster, Arbotect, Mertect, Mycozol, TBZ, Tecto, and Thibenzole), Imazalil (i.e. 1-(2-2,4-Dichlorophenyl)-2(2-propenyloxy-ethyl)-1Himidazol; e.g. Bromazil, Deccozil, Fungaflor, Freshgard, or Fungazil), Fenhexamide (e.g. Teldor), Pyrimethamil (e.g. Mitos) or a combination of Fludioxonyl and Cyprodinil (e.g. Switch) or a chemical equivalent thereof or a combination including same. Alternately, or additionally, the chemical antibiotic includes an antimicrobial agent or a pesticide.

The invention is further embodied by a method of inhibiting growth of a deleterious micro-organism on a portion of a plant, the method includes applying at least one time an agriculturally effective amount of a biologically pure culture of a yeast of the genus *Metschnikowia* to the portion of a plant. Preferably, the yeast of the genus *Metschnikowia* has all of the identifying characteristics of the species *Metschnikowia fructicola* identified as NRRL Y-30752 or of any strain thereof or of any mutant of such a strain.

The invention is further embodied by an article of manufacture which includes packaging material and a composition identified for use in protection of agricultural produce from a deleterious micro-organism. The article of manufacture includes, as an active ingredient, a biologically effective amount of yeast of biologically pure *Metschnikowia fructi-*

*cola* and further contains a carrier. Preferably, the article of manufacture further includes an applicator designed and constructed to apply the yeast to the agricultural produce. As used in this specification and the accompanying claims, the term "carrier" refers to any substance or diluent that does not cause significant irritation to agricultural produce or plants and does not abrogate the biological activity and properties of the administered active ingredient. As such, the term specifically includes, but is not limited to, aqueous solutions such as culture media, inert powders, and inert solvents (e.g. water).

The claimed yeast species, compositions and articles of manufacture including same and methods of use thereof are expected to find great utility in commercial agriculture. Their utility stems from their broad spectrum of activity against important pathogens and from the wide range of plants/fruits to which they may be efficaciously applied. In addition, Mf may be applied in the field, or concurrent with harvest, or during storage. Further, as demonstrated in examples herein below, Mf is useful under a wide variety of storage conditions. Thus, the present invention allows pre-harvest application of a benign yeast as a means of preventing post-harvest decay of agricultural produce.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

Example 1

Isolation of *Metschnikowia fructicola*

The novel yeast species *Metschnikowia fructicola* was isolated from the surface of grape berries (cv. Superior) grown in the central part of Israel. At various stages, individual berries were submersed in sterile distilled water in 100 ml beakers and shaken vigorously for 2 hours on rotary shaker at 120 rpm. Aliquots of 100 µl were removed from the wash liquid and plated on PDA (Potato Dextrose Agar; DIFCO Laboratories, U.S.A.) medium. Following 4–5 days of incubation, yeast colonies were picked randomly according to colony characteristics (color and morphology) and streaked individually on fresh medium to obtain biologically pure cultures. Cultures were further purified by repeated streaking on PDA. Identification and characterization of the new species was done at the Microbial Genomics and Bioprocessing center, USDA-ARS, Peoria, Ill., USA. *Metschnikowia fructicola* was deposited at the NRRL under the number Y-30752.

Example 2

Propagation of *Metschnikowia fructicola*

*Metschnikowia fructicola* is propagated under aerobic conditions at temperatures ranging from 5° C. to 37° C. Optimal growth temperature is 20–27° C. The growth is in liquid medium (nutrient broth; Droby et al., 1989) with a neutral pH. The cell density of the yeast reaches its maximum (stationary stage) growth in 24–48 hours. For laboratory and small scale tests growth in Erlenmeyer flasks containing the medium and shaken on a rotary shaker is suitable. For large scale and commercial tests, fermentation tanks and industrial growth media are preferred. The yeast cells are harvested by centrifugation using conventional laboratory or industrial centrifuges. One ordinarily skilled in the art of fermentation culture will be able to scale up culture volumes using suitable growth media and commercially available equipment.

Example 3

Laboratory Assay of Activity of *Metschnikowia fructicola* on Grapes and Cherry Tomato Individual grapes or cherry tomatoes were removed from clusters. Surface disinfection was accomplished by dipping for 1 min in 1% (v/v) sodium hypochlorite (pH 11.5). Disinfected fruit was mounted on masking tape strips glued to PVC pads within an incubation box. The fruit was punctured with a pin to a depth of 2 mm and 10 μl of an antagonist (*Metschnikowia fructicola* or as indicated) cell suspension were pippeted onto the wound site and left to dry for 1–2 hours. Fruit was then inoculated with 10 μl of conidial suspension of an appropriate fungal pathogen (*B. cinerea* or as indicated). Conidial suspensions were obtained from one-week-old pathogen cultures incubated at room temperatures. Spore concentration was adjusted to $1-5 \times 10^4$ conidia/ml. Each treatment was applied to three replicates of 7–10 individual fruit. Following the treatment, wet filter paper was placed in the incubation boxes which were covered with polyethylene to maintain high relative humidity. The percentage of decayed berries/fruits in each replicate was evaluated after 4–5 days at 20 C. This assay was employed in examples 16, 17, 26 and 28 described hereinbelow.

Example 4

Field Test of Activity of *Metschnikowia fructicola* on Grape

The efficacy of *Metschnikowia fructicola* and other yeast antagonists against bunch rot of wine and table grapes was evaluated on various varieties of grapes in vineyards located in the northern, central and southern coastal plains of Israel. Thompson Seedless and 'Superior Seedless' (table grapes) and 'Sauvignon blanc' (wine grapes) were tested. Experimental plots consisted of one to seven vines per treatment in the different experiments, arranged as randomized blocks with at least four replicates. The yeast antagonist and chemical standards (Mitos 0.25%) were applied weekly up to 4 times until run-off, with hand driven back-sprayer.

The incidence of decay (% decayed bunches) in the grape experiments in the field was determined on the day of harvest (field evaluation). Forty clusters were sampled from each plot and scored according to the causal agent of the decay and percentage of rot. For table grapes, the rot was also evaluated in storage. Approximately 3–5 Kg of grapes were harvested from each plot and packed in plastic bags which were wrapped in polyethylene bags to create high relative humidity. Rot development was evaluated after 3–4 weeks of storage at 0° C. followed by 4–7 days at 20° C. (cold storage ) or for 10 days at 20 (shelf life). $SO_2$ standard treatment was used as a comparison. Data summarized in FIGS. 12A and B indicates that Mf is comparable in its effectiveness to the chemical antifungal.

Example 5

*Metschnikowia fructicola* Inhibits Decay of Sweet Cherries

The effect of the yeast antagonists *Metschnikowia fructicola* (MF) of the present invention and *Candida oleophila* (I-182) on the development of postharvest decay on sweet cherries were tested at a concentration of $10^8$ cells/ml. Cherries were dipped for 1 min. in yeast cell suspensions, allowed to air dry and then stored under various conditions: up to 6 days at 24° C.; 30 days at 0° C. followed by 4 days at shelf life (room temperature); and 30 days at 0° C. under modified atmosphere (MA) packaging (P-Plus, Sidlaw Packaging, Bristol-UK) followed by 4 days of shelf life. The atmosphere in the bag used for MA packaging was determined by removing an aliquot of air and injecting it into a GC gas chromatograph with a TDC detector and a Poropak column (Supelco, Bellepenta, Pa., USA). Number of decayed berries was determined following the storage and shelf life period.

Figure 26:
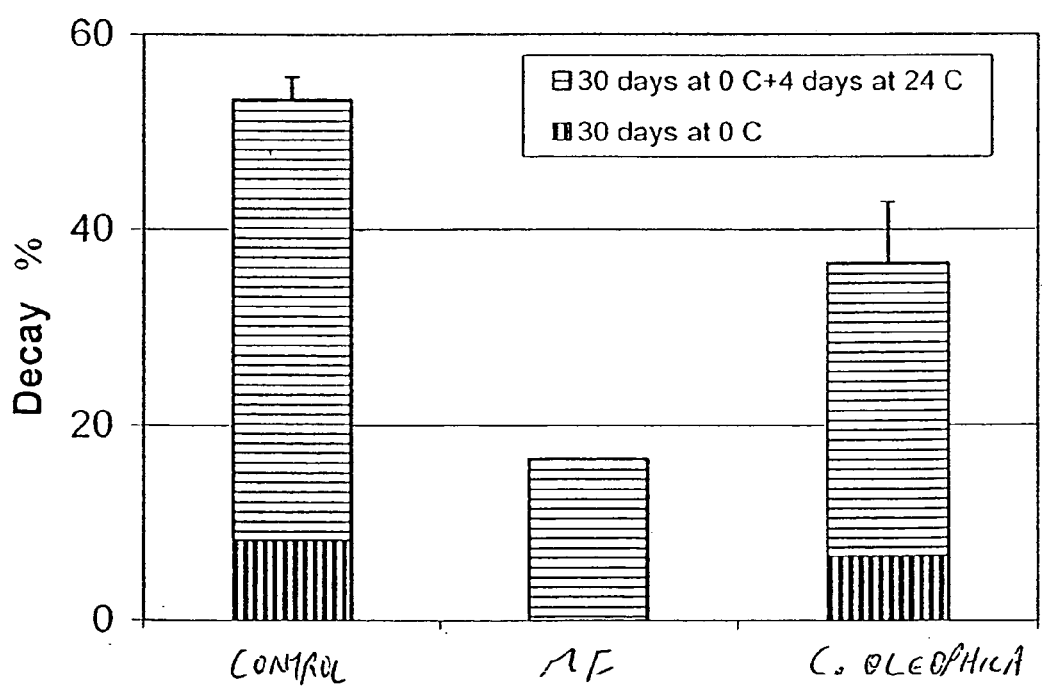
FIG. 26 is a histogram of % decayed fruits illustrating the ability of *Metschnikowia fructicola* (Mf; $10^8$ cells/ml) of the present invention and of *C. oleophila* to reduce natural decay from (*Botrytis cinerea*) on sweet cherry during and after cold storage (30 days at 0° C. and after an additional 4 days of storage at 24° C.).

Data, summarized in FIG. 26, indicate that Mf is more effective than *Candida oleophila*.

Example 6

Growth Characteristics of *Metschnikowia fructicola* under Refrigeration

In order to demonstrate that Mf is useful under conditions of cold storage, yeast cells were grown in Erlenmeyer flasks (50 ml media/100 ml flasks) containing liquid medium consisting of nutrient broth, yeast extract and D-glucose (NYDB: Droby et al., 1989) on rotary shakers placed in cold room at 4 C. Aliquots (1 ml) were aseptically withdrawn from the growth medium at 1 day intervals, serially diluted and plated on solid medium (NYDA: Droby et al., 1989). After 3–4 days incubation at 25° C. the number of colonies growing on the medium were counted and expressed as Log number of cells/ml. Data are summarized in FIG. 1. Mf grew much faster than *M. raukaufii* or *K. thermotolerance* during 6 days under refrigeration. This indicates that MF is more suited to biological control of post harvest rot under cold storage conditions than *M. reukaufii i* or *K. thermotolerance*.

Example 7

*Metschnikowia fructicola* Colonizes Wounds in Citrus Fruit Peel

Figure 2:
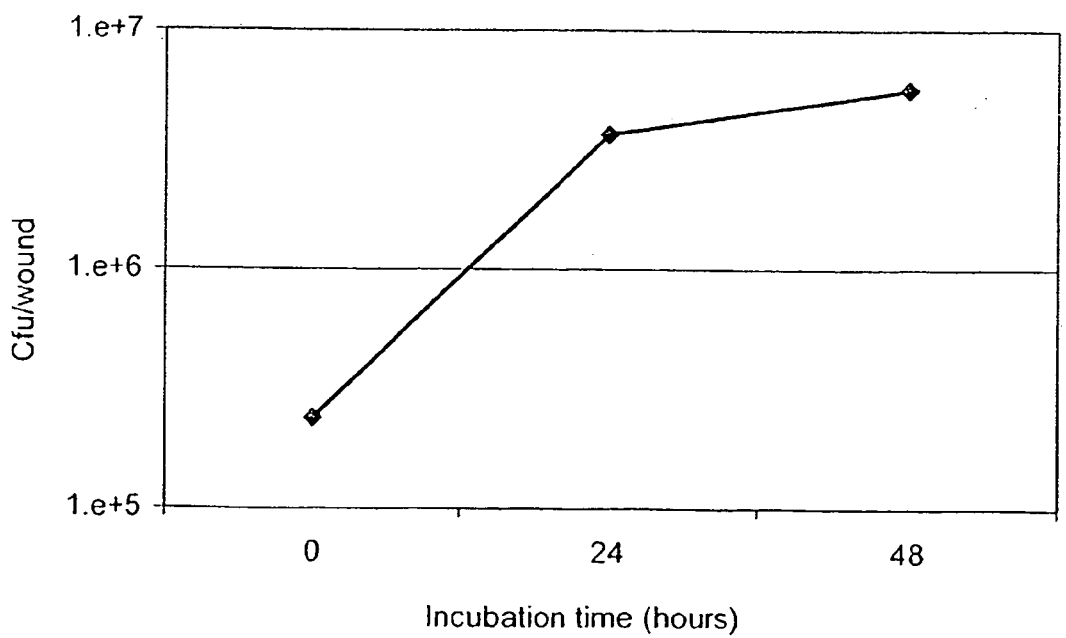
FIG. 2 is a graph of colony forming units (cfu) per wound as a function of time for the yeast *Metschnikowia fructicola* (Mf) of the present invention in citrus fruit surface wounds.

In order to demonstrate that Mf is capable of protecting wounds in a fruit surface, its ability to colonize and grow at the wound site on a fruit surface was tested. The fruit was wiped with 95% ethanol and wounded (3×3 mm wounds) using a dissecting needle at four sites. An aliquot (20 μl) of the yeast cell suspension ($2 \times 10^6$ cells/ml) was pipetted into each wound. The fruit was incubated at 20° C. and at intervals of 1, 24 and 48 h, a 5×5 mm piece was cut from each of the four wounds and vigorously shaken in 10 ml of sterilized distilled water for 1 h. Serial one-tenth dilutions of the washing liquid werte prepared and 100 μl of each dilution was plated on NYDA. The number of colonies was counted during 48 h of incubation at 25° C. Each fruit containing four wounds represented a single replicate, and each treatment contained 6 replicates. Data (summarized in FIG. 2) are presented as cfu (colony forming units) of *Metschnikowia fructicola* (Mf)/wound. Results indicate that Mf is capable of replicating and colonizing a fruit surface wound at room temperature.

Example 8

Colonization by *Metschnikowia fructicola* Protects s Wounds in Citrus Fruit Peel by Competition for Nutrients In order to establish that Mf is capable of competing for nutrients surface sterilized grapefruits were wounded around the stem end, with three wounds per fruit. Each wound was made by inserting a dissecting needle to a depth of 3 mm. Thirty μl of a water suspension of the antagonist Mf cells was pipetted into each wound. One to two hours later, 20 μl of a spore suspension of *P. digitatum* ($5 \times 10^4$ spores/ml) was applied to each wound. Macerated grapefruit peel was prepared from water soaked peel at the margins of *P.*

Figure 3:
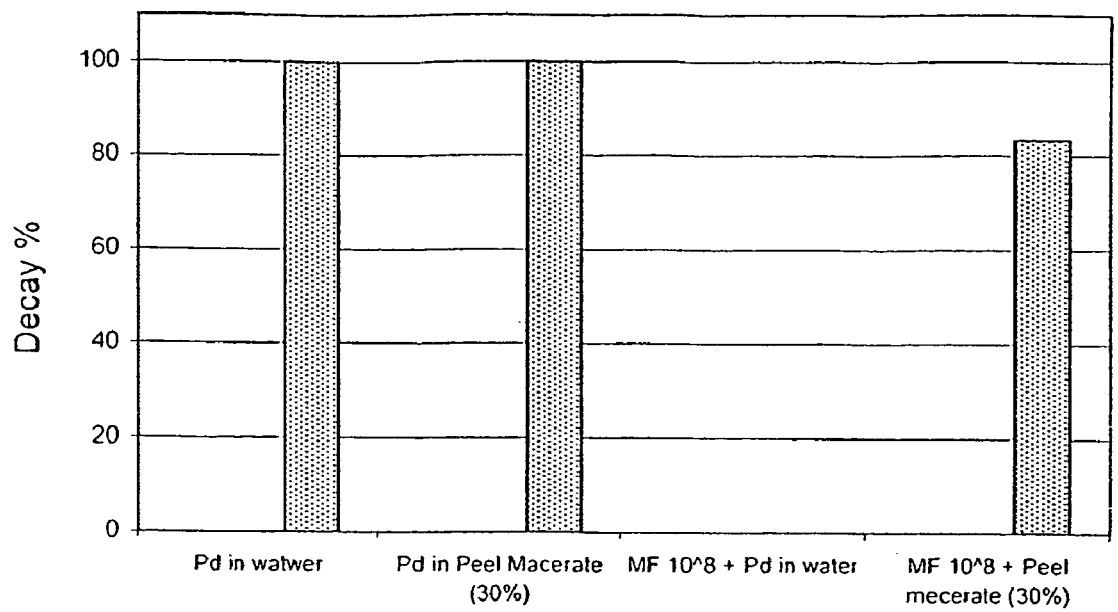
FIG. 3 is a histogram illustrating reduction of % decay caused by *Penicillium digitatum* (Pd) infection of red grapefruit by *Metschnikowia fructicola* (Mf) of the present invention and the effect of addition of exogenous nutrients obtained from macerated grapefruit peel.

*digitatum* induced lesions on grapefruit. Ten grams of the peel was homogenized in blender, diluted with distilled water to 20% strength and then autoclaved. Aliquots of concentrated spore suspension of *P. digitatum* were added to the peel macerate to give a final spore concentration of $5 \times 10^4$ spores/ml, which was used to inoculate fruit wounds pretreated with a cell suspension of *Metschnikowia fructicola* (Mf). Control fruits were inoculated with a similar spore suspension of *P. digitatum* in water. Each fruit was inoculated at three sites. Twelve fruits were used for each treatment to give a total of 36 inoculation sites per treatment. Percent wound infection was measured after 5 days incubation at 24° C. Data are summarized in FIG. 3. Results indicate that *Metschnikowia fructicola* (Mf) successfully protects against *Penicillium digitatum* (Pd) infection of red grapefruit, but fails to do so in the presence of supplementary nutrients extracted from the peel. These results clearly indicate that competition for nutrients plays a major role in Mf's protective capability.

Example 9

Figure 4:
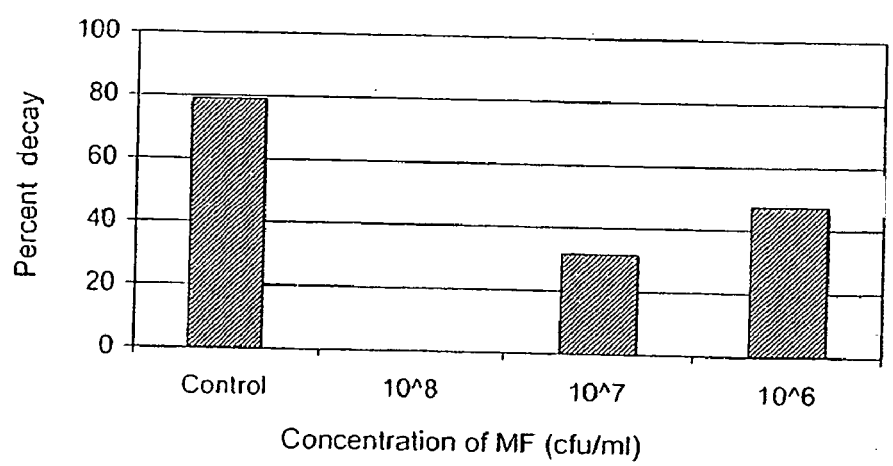
FIG. 4 is a histogram illustrating that response of green mold decay, caused by *P. digitatum*, on grapefruit to *Metschnikowia fructicola* (Mf) of the present invention is concentration dependent.

*Metschnikowia fructicola* Protects against Green Mold Decay in a Concentration Dependent Manner In order to demonstrate that the protective effect of Mf is concentration dependent, surface sterilized grapefruits were wounded around the stem end, as in Example 8. Thirty microliters of a water suspension of the antagonist Mf cells was pipetted into each wound. One to two hours later, 20 μl of a spore suspension of *P. digitatum* ($5 \times 10^4$ spores/ml) was applied to each wound. Percent of decay was determined 1 week after incubation in humid conditions in plastic trays at 24 C. Twelve fruits per treatment were used. Data are summarized in FIG. 4. Results indicate that complete inhibition of decay was achieved at a concentration of $10^8$ cfu with partial protection achieved at $10^7$ and $10^6$ cfu.

Example 10

*Metschnikowia fructicola* does not Produce Antibiotics

Figure 5:
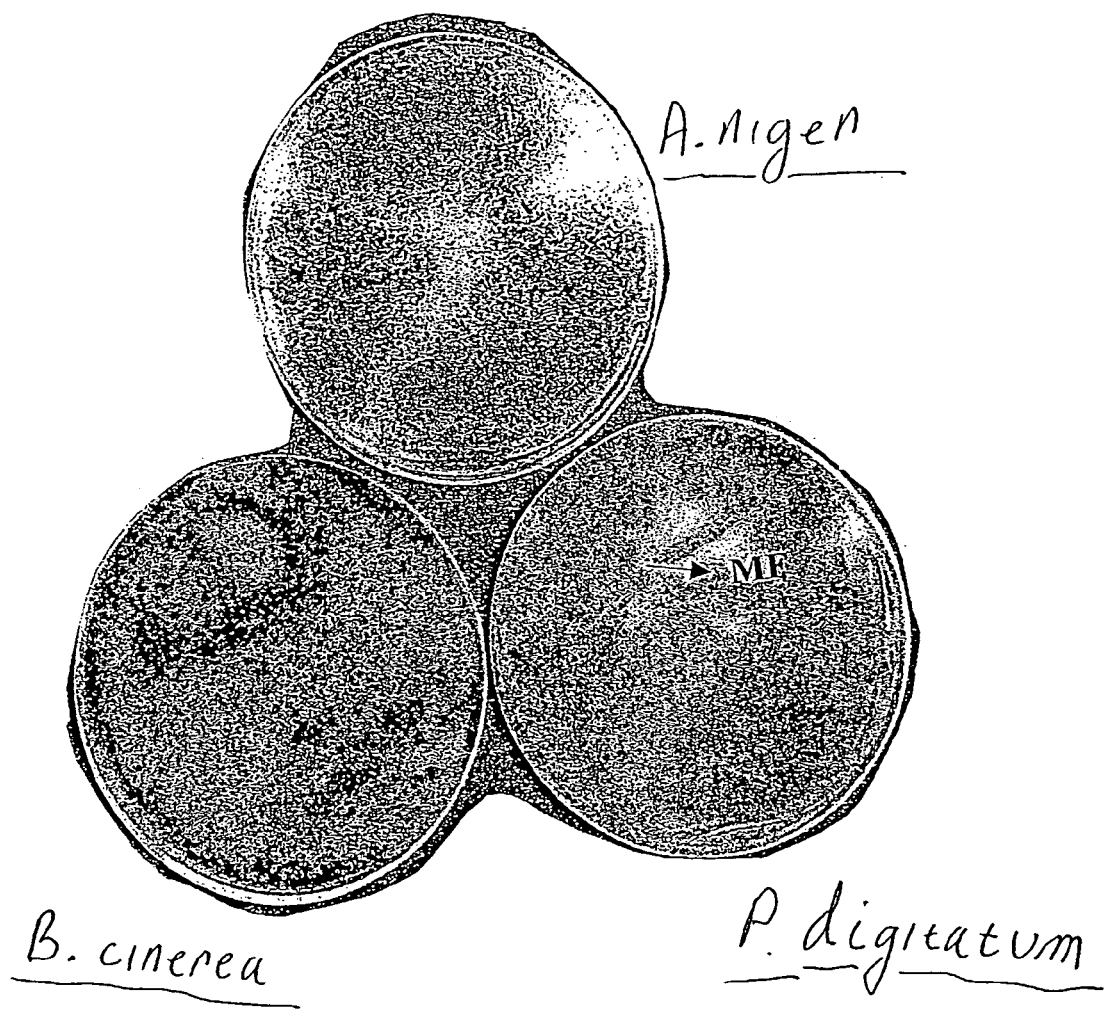
FIG. 5 is a photo of Petri dishes illustrating lack of long distance inhibition of different postharvest pathogens by *Metschnikowia fructicola* (Mf) of the present invention in solid growth medium.

Because there is great concern about widespread use of antibiotics, the mechanism by which mf protects fruit was examined. In order to determine if the ability of Mf to protect fruit is mediated by antibiotic production, Mf was screened against three major fruit pathogens (*Aspergillus niger, Botrytis cinerea, Penicillium digitatum*). Yeast cells were streaked on one side of PDA plates. Agar plug (0.5×0.5 mm) containing the fungal culture was placed on the other side of the plate and then plates were incubated at 25 C for one week. Representative results are presented in FIG. 5. No inhibition of the three tested pathogens was observed. This demonstrates that Mf does not produce diffusible antibiotics.

Example 11

Inhibition by *Metschnikowia fructicola* Correlates to Chitinase Activity

To test relative biocontrol efficacy of Mf and other yeasts, apples were washed with tap water, dried, uniform wounds of 4 mm depth and 2–3 mm in diameter were made on the side of each fruit. Each wound was inoculated with 40 μl of yeast suspension at a concentration of $10^8$ cells/ml. After 3 h, 20 μl of suspension containing $10^4$ spore/ml of *P. expansum* were added to each wound. Treated apples were stored at ambient temperature and high relative humidity Percent wound decay was determined 10 days after inoculation. The number of infected (decayed) woun eachds was determined. Each treatment consisted of 3 replicates of 10 fruits. Each fruit was wounded at one location.

Figure 6:
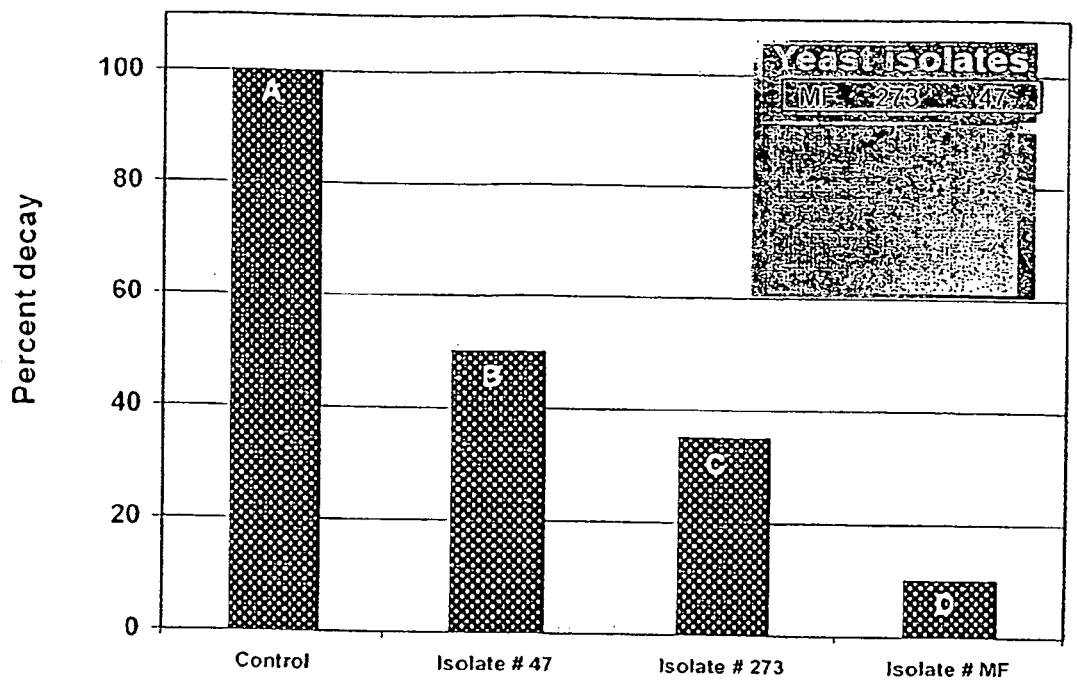
FIG. 6 is a histogram illustrating the correlation between of chitinolytic activity of *Metschnikowia fructicola* (Mf) of the present invention and yeast isolates #47 and #273 with their biocontrol activity against *Penicillium expansum* on apples. The inset shows that the yeast Mf produces high amounts of chitinases relative to the other yeast isolates.

Results are summarized in FIG. 6. Detection of chitinase activity (insert) was performed as follows: Sodium dodecyl sulfate (SDS)-PAGE was performed at pH 8.9 by using a 15% (w/v) polyacrylamid gel containing 0.01%(w/v) glycol chitin as substrate and 0.1% (w/v) SDS. The crude enzyme preparation, obtained from the supernatant of the yeasts liquid cultures were boiled for 2 min in 10% (w/v) sucrose and 2% SDS in 125 mM Tris-HCl (pH 6.7). Elecrophoresis was run at room temp. for 1.5 h at 20 mA. After Elecrophoresis, the gel was incubated overnight at 37 C on rotating apparatus in 200 ml of 100 mM sodium acetate buffer (pH 5). At the end of incubation period the gel was stained with 0.01% (w/v) Calcoflour white M2R in 0.3 M Tris-HCl (pH 8.9) for 5 min, and destained by incubating the gel in 100 ml of distilled water with a gentle shaking for 2 h. Lytic zones were visualized by placing the gel on under UV light. Because Calcoflour white M2R does not stain hydrolyzed chitin, black bands in the Mf lane indicate that the yeast Mf produces high quantities of chitinase compared with the other tested yeasts Results presented in FIG. 6 clearly indicate that the superior ability of Mf to protect apples against *Penicillium expansum* is well correlated to chitinolytic activity. Other yeasts lacking this activity (isolates #47 and #273) were less effective against *Penicillium expansum*. This data indicate that chitinolytic activity, as well as competition, contribute to the protective effect of Mf.

Example 12

Effect of Temperature on *Metschnikowia fructicola*

The ability Mf to remain viable after prolonged exposure to temperatures ranging from 0 to 42° C. was tested on solid potato dextrose agar plates. Mf was lightly streaked on the surface of PDA plates and incubated at the indicated temperatures for 4 days and then moved to 25° C. for an additional 4 days. Growth was evaluated visually. Results are summarized in Table 1.

TABLE 1

Growth of the yeast *Metschnikowia fructicola* (Mf) at different temperatures.

| Initial 4 day incubation at | Incubation Time (days) at 25° C. After initial incubation | | |
|---|---|---|---|
| Temp. ° C. | 4+ | 4 | 3 |
| 0 | − | − | +++ |
| 5 | + | + | +++ |
| 10 | ++ | ++ | +++ |
| 20 | +++ | +++ | +++ |
| 28 | +++ | +++ | +++ |
| 37 | − | − | +++ |
| 42 | − | − | − |

No growth: −
Weak Growth: +
Moderate Growth: ++
Normal Growth: +++

These results indicate that Mf remains viable after storage at 0–5° C. and that Mf is able to withstand temperatures lower than 37° C.

Example 13

*Metschnikowia fructicola* Acts Synergistically with Chemical Fungicides

Figure 7:
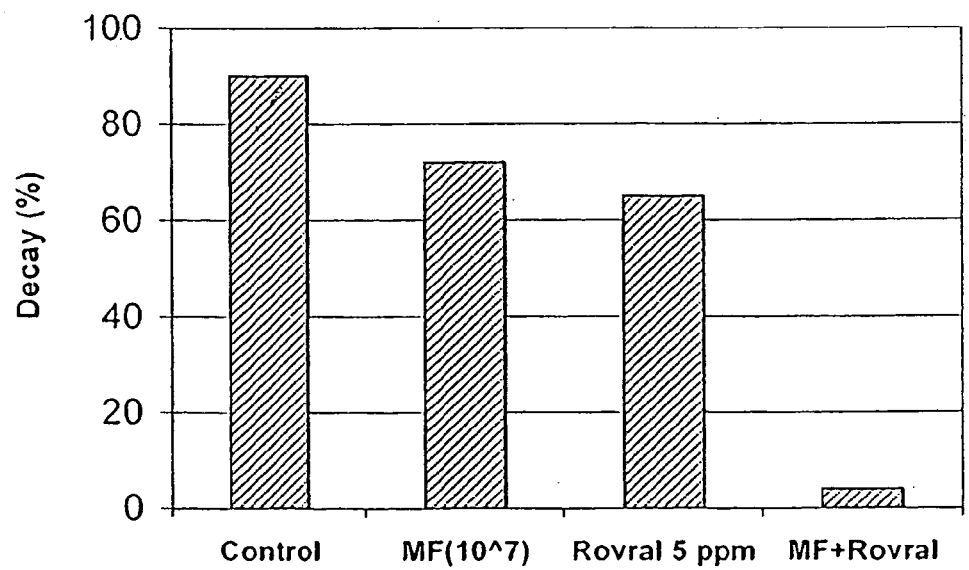
FIG. 7 is a histogram illustrating the synergistic effect of the yeast *Metschnikowia fructicola* (Mf) of the present invention with the fungicide Rovral (Iprodione) against *Botrytis cinerea* of table grapes.

Individual grapes (cv. Superior; table grapes) were surface disinfected by dipping for 1 min in 1% (v/v) sodium hypochlorite (pH 11.5) and mounted on masking tape strips glued to PVC pads within an incubation box. The grapes were punctured with a pin to a depth of 2 mm and 20 µl of an antagonist cell suspension ($10^7$ cells/ml) or Rovral brand of Iprodione (5 ppm) or both were pippeted onto the wound site and left to dry for 1–2 hours. Grapes were then inoculated with 10 µl of conidial suspension of *B. cinerea* obtained from one-week-old pathogen cultures incubated at room temperatures. Spore concentration was adjusted to $1–5 \times 10^4$ conidia/ml. Each treatment was applied to three replicates of 7–10 grapes. Following the treatment, wet filter paper was placed in the incubation boxeswhich were covered with polyethylene to maintain high relative humidity. The percentage of decayed grapes in each replicate was evaluated after 4–5 days at 20° C. Results, summarized in FIG. 7, indicate that there is significant synergy between Rovral brand of Iprodione and Mf.

Example 14

*Metschnikowia fructicola* is Compatible with a Varirty of Agrochemicals

In order to establish that Mf is suitable for combination with a variety of commonly employed chemical pesticides, ten percent strength of liquid medium (NYDB) with various concentrations of common agrochemicals added was inoculated with a cell suspension of Mf (25 ml of $10^9$ cell/ml) and incubated on a rotary shaker at room temperature. The following commercially available agrochemicals were employed: TBZ (0.02%); Teldor (0.015%); Mitos (0.025%); Rovral (0.02%); Switch (0.01%); and Imazalil (0.005%). Samples were aseptically withdrawn from the at 0 time, 24 h and 48 h of incubation. Samples were serially diluted and aliquots of 30 µl of the dilutions were plated on PDA. Plates were incubated at 25° C. for 3–4 days and colony forming units (CFU) were counted.

Figure 8:
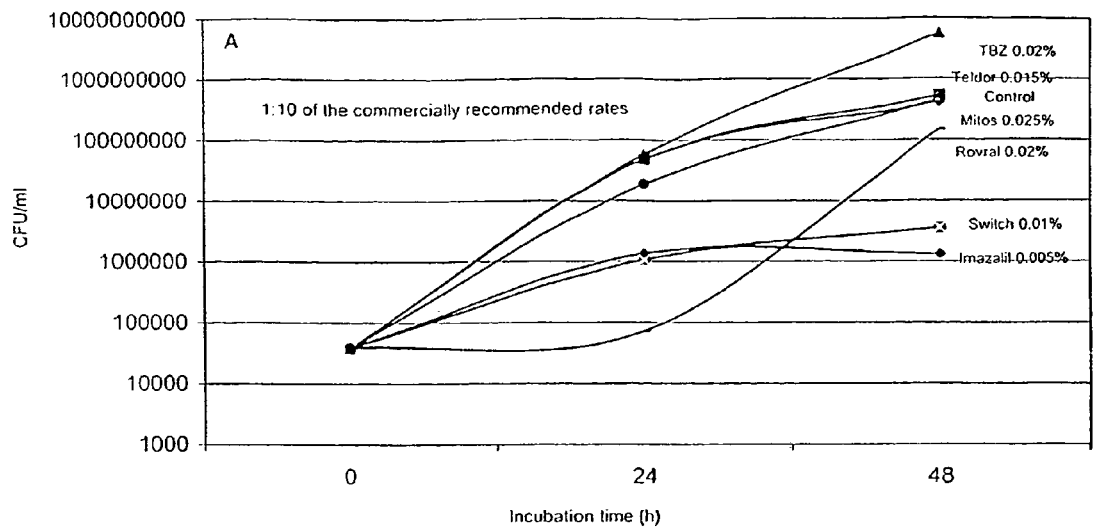
FIG. 8 is a graph of cfu as a function of time for *Metschnikowia fructicola* (Mf) of the present invention with various fungicides used to control *Botrytis cinerea* and *Penicilliun* sp. Data presented indicate that Mf is compatible/unaffected- with tested fungicides.

Results, summarized in FIG. 8, indicate that MF is not affected by the tested agrochemicals, even fungicides except Switch (0.01%) and Imazalil (0.005%) which slowed, but did not prevent, its growth

Example 15

*Metschnikowia fructicola* Survives under Field Conditions

In order to demonstrate that that Mf is more suited for use in the field than others yeast strains, grapes were collected from experimental plots designated to evaluate the efficacy of the yeast antagonist Mf in controlling pre and postharvest rots of table grapes in the central coastal area of Israel (Truman). Weekly spraying of the yeasts (starting from 21/6) at concentration of $10^8$ cells/ml using 231 (*Metschnikowia reukafii*), 414 (*Kluyveromyces thermotolerance*) and Mf was conducted. Grapes were collected on the first spraying date, after the clusters had dried and thereafter before each spray.

Figure 9:
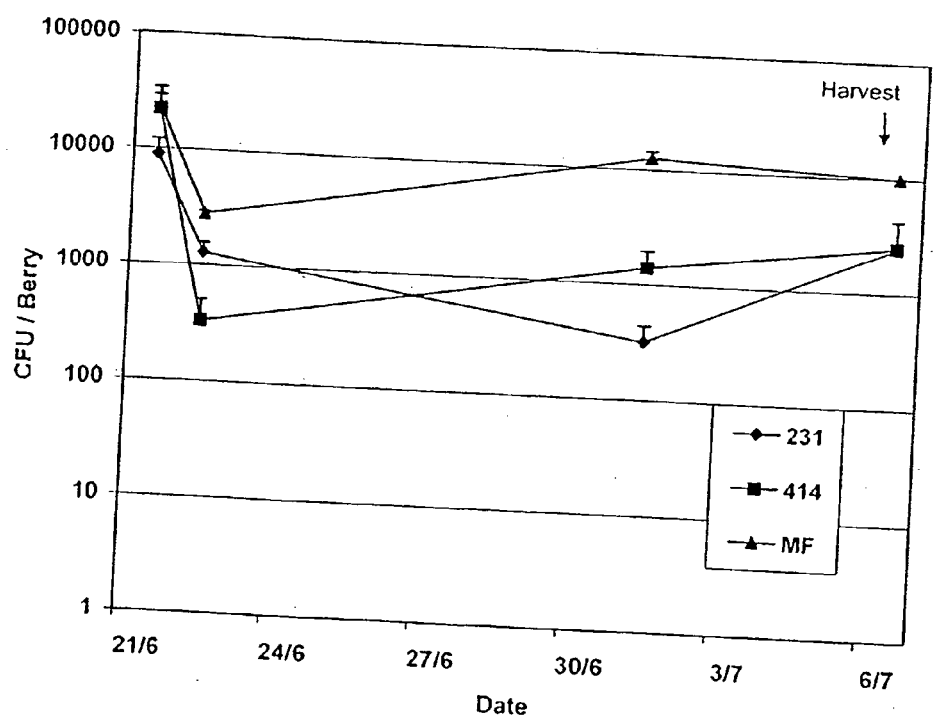
FIG. 9 is a graph of cfu/berry as a function of time for *Metschnikowia fructicola* (Mf) of the present invention, *Metshnikowia reukafii* (231) and *kluyveromyces thermotolerance* (414) on table grapes (cv. Superior) between field application and harvest.

At each collection, five grapes per plot were sampled aseptically into 150 ml sterile plastic cups containing 20 ml of water and shaken on a rotary shaker at 200 rpm for 1 h. After 1:10 serial dilutions, 20 ul of each dilution were plated in Petri dishes containing Basal yeast agar medium (BYA) containing 20 g glucose, 1 g yeast extract, 10 g protease peptone and 15 g agar amended with 250 mg Penicillin G (to suppress growth of bacteria) in 1 liter of distilled water. The Petri dishes were incubated at room temperature for 3–4 days, after which the number of colonies were counted. Yeast viability is expressed as CFU/berry. Results, summarized in FIG. 9, indicate that *Metschnikowia fructicola* (Mf) survives better in the field than *Metshnikowia reukafii* (231) or *kluyveromyces thermotolerance* (414) on table grapes (cv. Superior).

Example 16

*Metschnikowia fructicola* Inhibits Growth of *Aspergillus niger* and *Botrytis cinerea* on Grapes In order to show that Mf is effective against important grape pathogens, individual grapes were removed from clusters, surface disinfected by dipping for 1 min in 1% (v/v) sodium hypochlorite (pH 11.5) and mounted on masking tape strips as described hereinabove. The grapes were punctured with a pin as described hereinabove and an antagonist cell suspension was applied to the wound site and left to dry as described hereinabove. 30 µl of cell suspension of each strain at concentration of $10^8$ cell/ml was used. Grapes were then inoculated with 10 µl of conidial suspension of *Aspergillus niger* (FIG. 10) or *Botrytis cinerea* (FIG. 11). Conidial suspensions prepared and spore concentration was adjusted as described hereinabove.

Each treatment was applied to three replicates of 7–10 grapes. Following the treatment, wet filter paper was placed in the boxes which were covered with polyethylene to maintain high relative humidity. The percentage of decayed grapes in each replicate was evaluated after 4–5 days at 20° C.

Figure 10:
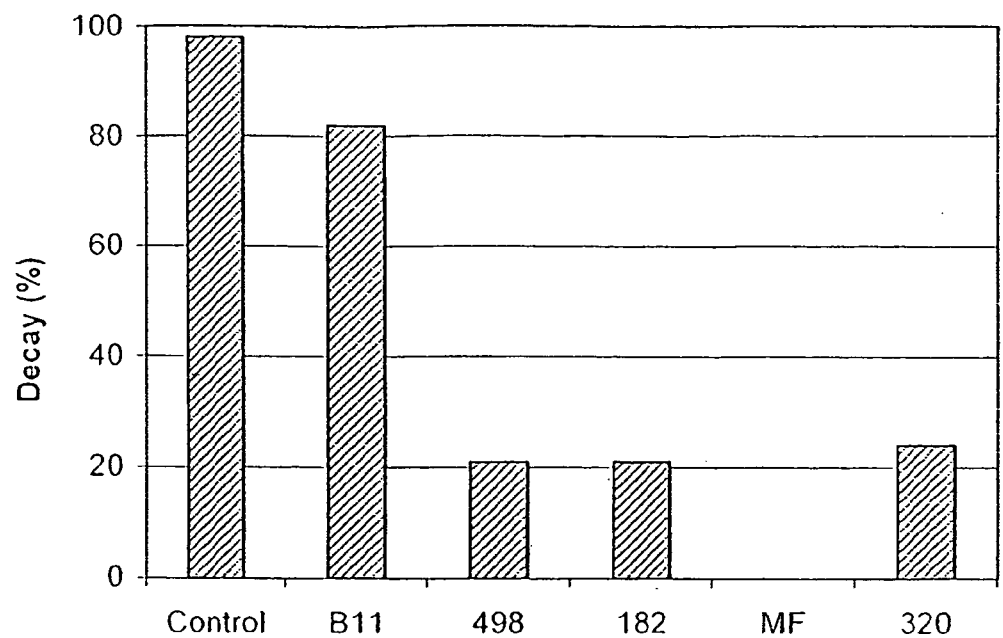
FIG. 10 is a histogram comparing the effect of *Metschnikowia fructicola* (Mf) of the present invention to other yeast isolates on decay of table grapes caused by *Aspergillus niger*.
Figure 11:
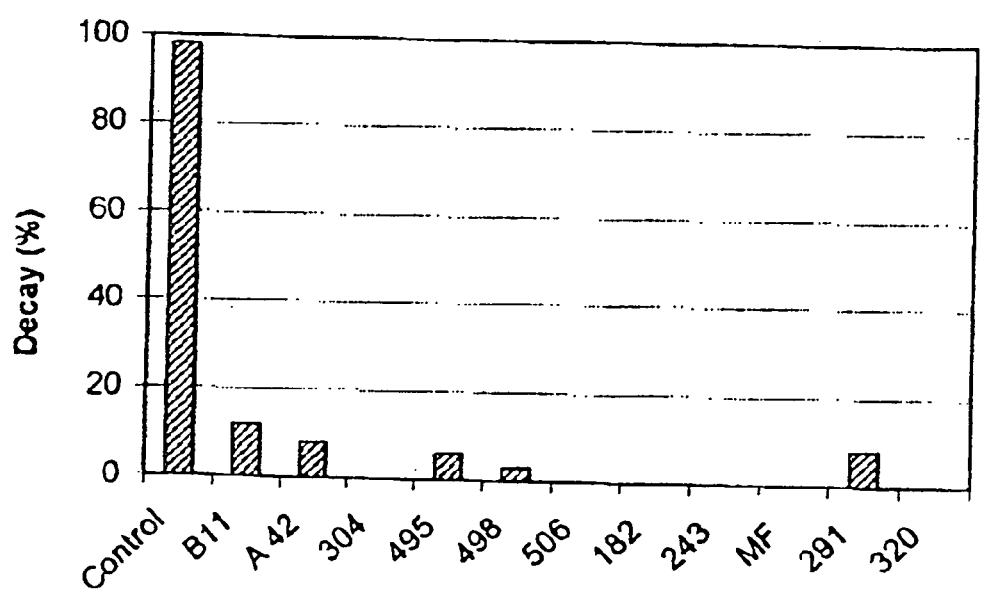
FIG. 11 is a histogram comparing the effect of *Metschnikowia fructicola* (Mf) of the present invention to other yeast isolates on decay caused by *Botrytis* of table grapes in a laboratory assay.

FIGS. 10 and 11 clearly indicate that Mf is the most effective of the assayed yeast strains in controlling growth of *Aspergillus niger* and *Botrytis cinerea* on wounds of table grapes. In FIG. 11 A42 indicates *Candida guilliemondii*, 495 indicates *Debaryomyces hansenii* and strains 243 and 509 are unidentified yeasts.

Example 17

*Metschnikowia fructicola* Controls Bunch Rot of Grapes

In order to further demonstrate the superior qualities of Mf in the field, the efficacy of Mf relative to a chemical fungicide spray (mitos) against bunch rot of wine and table grapes was evaluated on various varieties in vineyards located in the northern, central and southern coastal plains of Israel on Thompson Seedless and 'Superior Seedless' (table grapes) and 'Sauvignon blanc' (wine grapes).

Experimental plots consisted of one to seven vines per treatment in the different experiments, arranged as randomized blocks with at least four replicates. The yeast antagonist and chemical controls were applied weekly 4 times until run-off, with a hand driven back-sprayer. The incidence of decay in the wine and table grape experiments was determined on the day of harvest. Forty clusters were sampled from each plot and scored according to the causal agent of the decay and percentage of rot. In the table grapes experiments, the rot was also evaluated in storage. Approximately 3–5 Kg of grapes were harvested from each plot and packed in plastic bags which were wrapped in polyethylene bags to create high relative humidity. Rot development was evaluated after 3–4 weeks of storage at 0° C. followed by 4–7 days at 20° C.

Figure 12A:
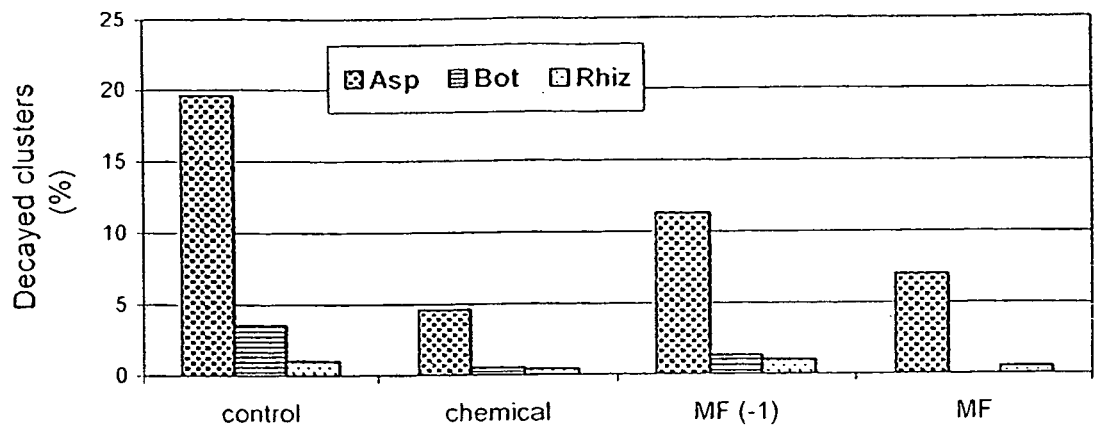
FIGS. 12A and B are histograms of disease index and % decayed clusters respectively and the effect of *Metschnikowia fructicola* (Mf) of the present invention at $10^8$ cells/ml applied in the field as compared to untreated controls and chemically treated grapes. Growth of pathogens *Aspergillus*, *Botrytis* and *Rhizopus* is shown.
Figure 12B:
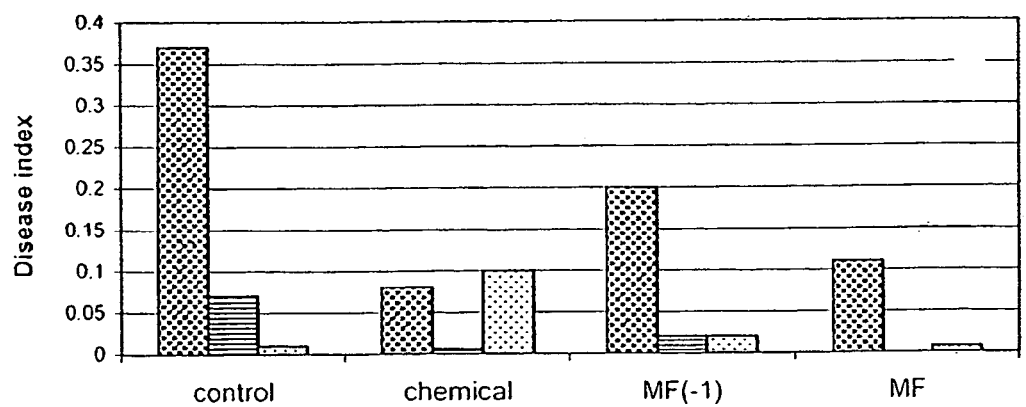

FIGS. 12A and 12B clearly show that Mf applied to wine grapes at a concentration of $10^8$ cells/ml was more effective than Mitos (0.25%) in controlling bunch rot caused by *Aspergillus, Botrytis* and *Rhizopus*.

Figure 13A:
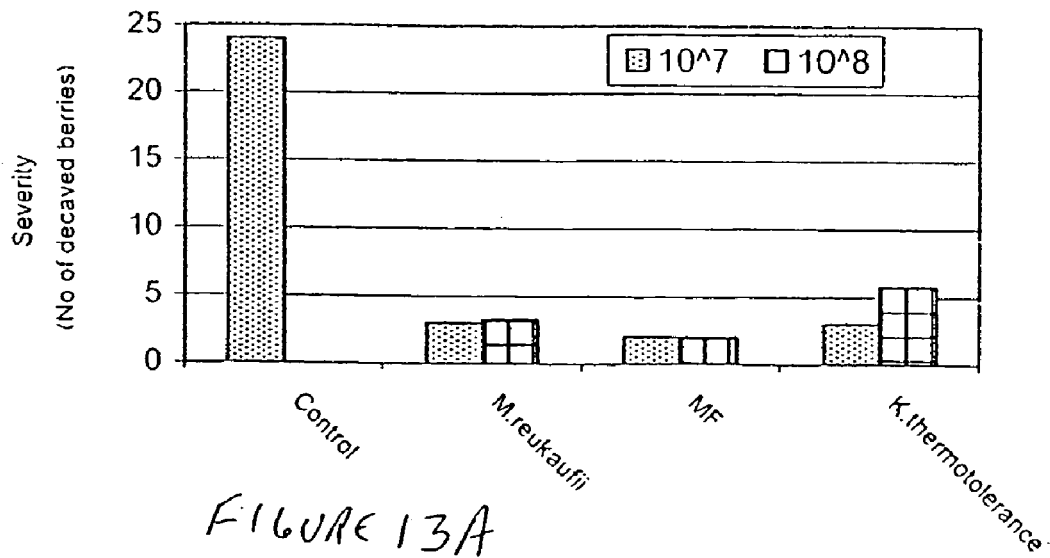
FIGS. 13A and B are histograms of disease index and % decayed clusters respectively as a result of *Rhizopus* infection in the field and the effect of *Metschnikowia fructicola* (Mf) of the present invention relative to *M. raukaufili* and *K. thermotolerance*.
Figure 13B:
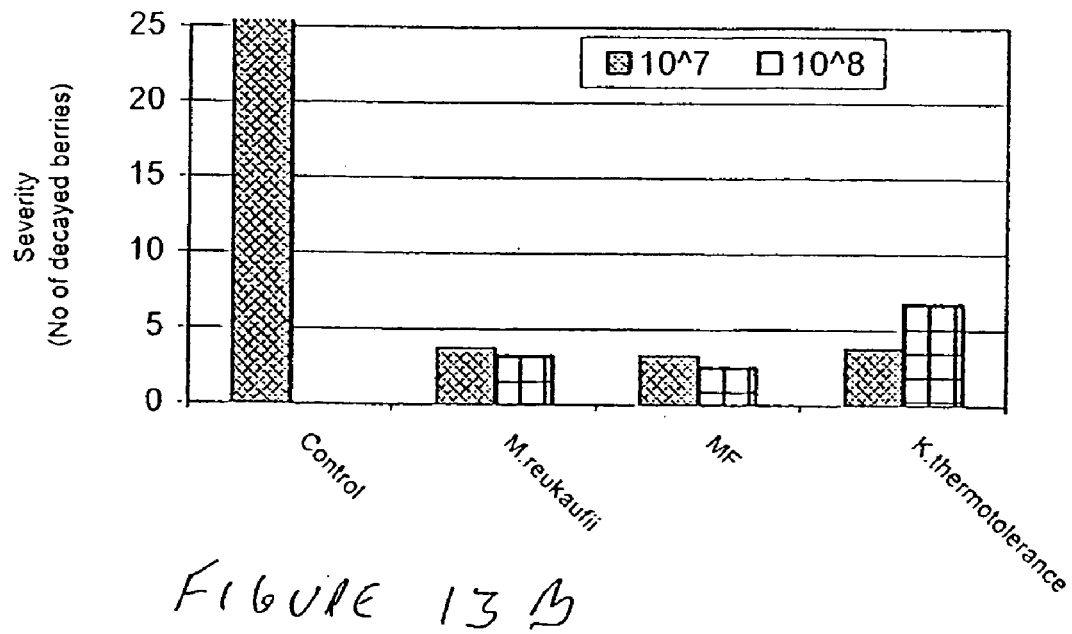

FIGS. 13A and 13B clearly show that preharvest application of the yeast MF at concentrations as low as $10^7$ cells/ml was more effective in controlling *Rhizopus* rot developed on grape bunches in the filed than *M. raukaufii* or *K. thermotolerance*.

Figure 14:
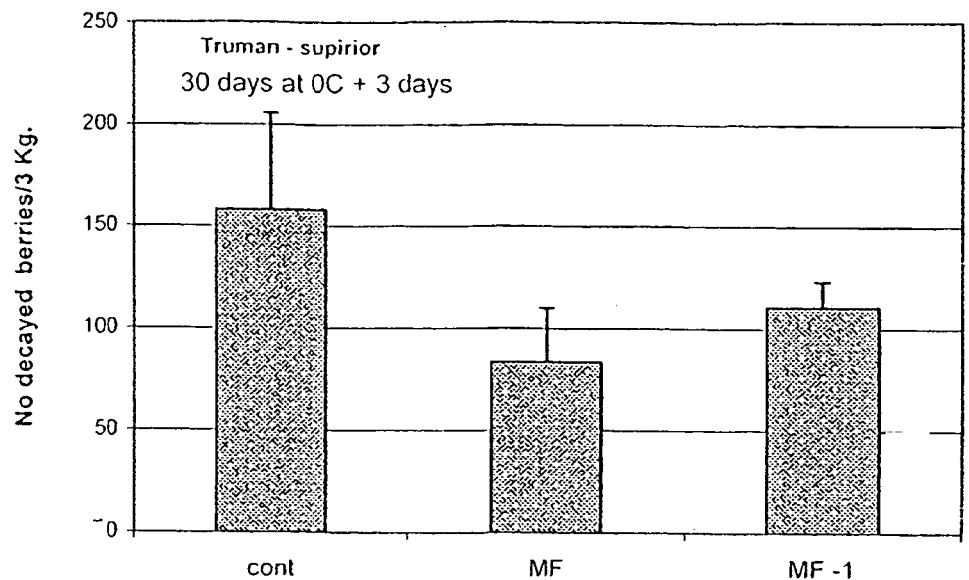
FIG. 14 is a histogram showing decayed berries/3 Kg. for untreated (control) and grapes treated in the field with *Metschnikowia fructicola* ($10^8$ cells/ml (MF) and $10^7$ cells/ml ($MF^{-1}$)) of the present invention. Decay was caused by *Botrytis cinerea* which developed postharvest.

FIG. 14 clearly shows that Mf applied to table grapes (Cv. Superior) . . . at concentrations of $10^8$ (Mf) and $10^7$ ($Mf^{-1}$) cells/ml reduced disease severity after cold storage.

Figure 15:
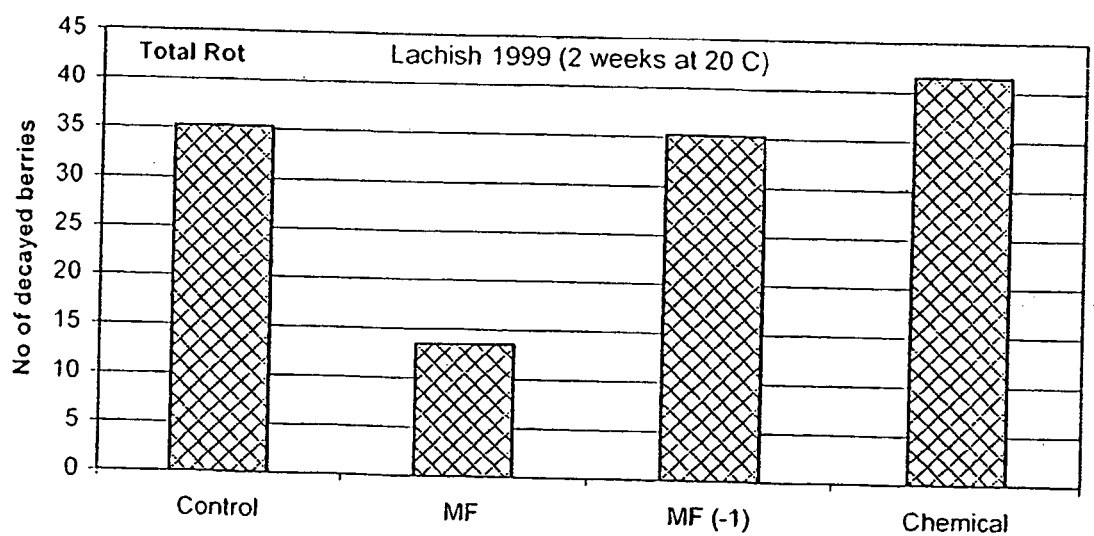
FIG. 15 is a histogram showing decayed berries/Kg as a result of storage comparing untreated (control) and grapes treated with *Metschnikowia fructicola* ($10^8$ (MF) cells/ml and $10^7$ ($MF^{-1}$) cells/ml) of the present invention. Decay was caused by *Botrytis cinerea, Rhizopus stolonifer* and *Aspergillus niger*.

FIG. 15 clearly shows that Mf applied to table grapes (Cv. Thompson) at concentrations of $10^8$ and $10^7$ cells/ml prior to harvest was superior to chemical treatment with one $SO_2$ saturated pad per carton in controlling bunch rot caused by Aspergillus for up to 2 weeks of storage at 20° C.

Figure 16:
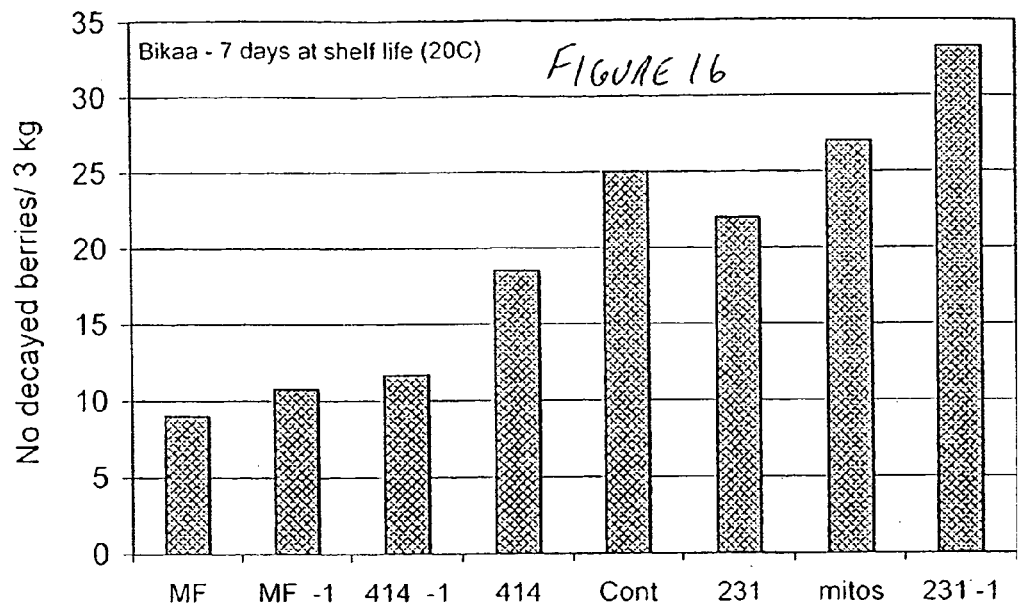
FIG. 16 is a histogram comparing efficacy of the yeast *Metschnikowia fructicola* (Mf) of the present invention to *Metschnikowia reukafii* (231) and *Kluyveromyces thermotolerance* (414) and Mitos in controlling damage to grapes in the field caused by *Aspergillus* and *Botrytis* and *Rhizopus* pathogens.

FIG. 16 clearly shows that Mf is more effective than *Metchnikowia reukafii* (231), *Kluyveromyces thermotolerance* (414) or mitos in controlling damage to grapes caused by *Aspergillus+Botrytis+Rhizopus* pathogens.

In summary, these results indicate that use of Mf as a fungal antagonist is as effective as commonly employed chemical fungicides for control of pre and postharvest bunch rot in grapes.

Example 18

*Metschnikowia fructicola* Protects Flower Bulbs from a Variety of Pathogens

Figure 17A:
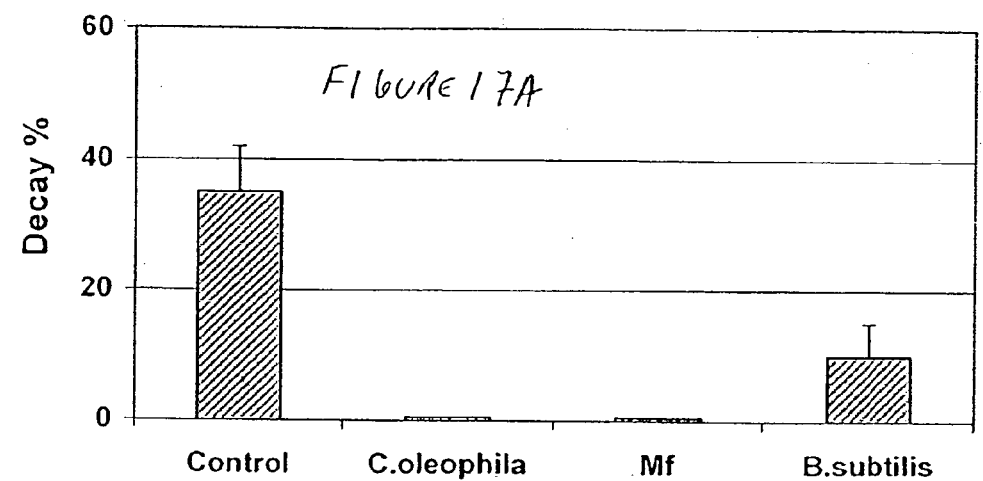
FIGS. 17A and B are histograms illustrating efficacy of the yeast *Metschnikowia fructicola* (Mf) of the present invention, as compared to *C. oleophila* and *B. subtilis* in controlling *Fusarium oxysporum* rot on Easter Lilly bulbs.
Figure 17B:
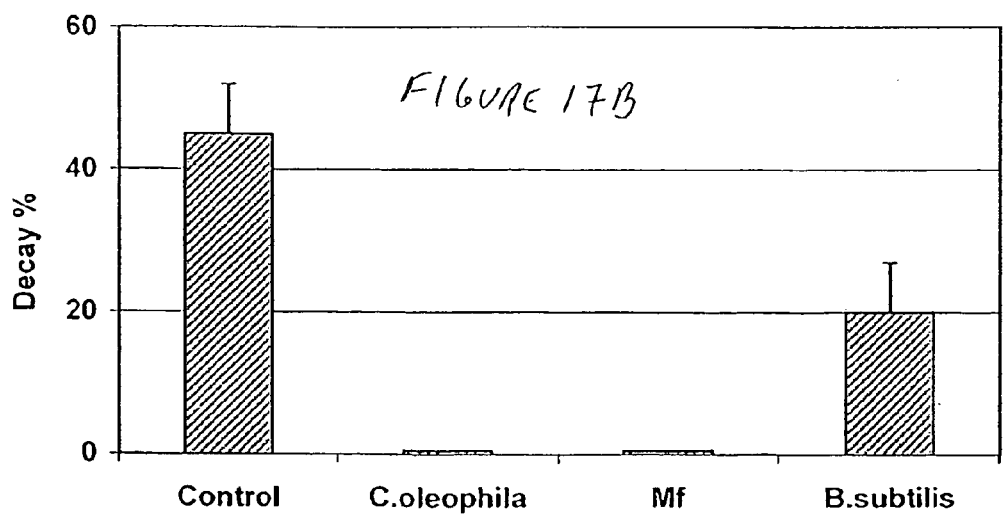

Easter Lilly bulbs were injured at one site and dipped for 1 min in cell suspension of the yeast *Metschnikowia fructicola* (Mf), *Candida oleophila* or *Bacillus subtilis* at concentration of $10^8$ cells/ml, allowed to dry for 2–3 h and inoculated with spore suspension of *Fusarium oxysporum* ($10^5$ spores/ml; FIGS. 17A and B) or of *Penicillium hirsutum* ($10^5$ spores/ml; FIGS. 18A and B) by spraying the bulbs until run off. Bulbs sprayed with water were used as controls. Percent of infected bulbs was determined following storage period of two weeks at 9 C followed by 1 week of storage at 20 C.

Data summarized in FIGS. 17A and B show that Mf is more efficient in controlling *Fusarium oxysporum* rot on Easter Lilly bulbs than *B. subtilis*. Data summarized in FIGS. 18A and B show that Mf is more efficient in controlling *Penicillium hirsutum* rot on Easter Lilly bulbs than *C. oleophila*. In summary, Mf offers broader protection for lily bulbs than *C. oleophila* or *B. subtilis*.

Example 19

*Metschnikowia fructicola* Inhibits Natural Infection of Stone Fruit

In order to evaluate the effect of the yeast antagonists *Metschnikowia fructicola* (Mf) and *Candida oleophila* on development of natural decay of stone fruit, 'Flavortop' nectarines were employed. Fruit was dipped into a cell suspension ($10^8$ cells.$ml^{-1}$) of either Mf or *Candida oleophila*. Fruit dipped in tap water (20° C.) served as a negative control. Treated fruit was stored at 0° C. for 30 days and then held for 10 days at 24° C. At the end of this second incubation, decay incidence was determined. In all experiments, each treatment included three replicates of 30 fruit each.

Results summarized in FIG. 19 indicate that Mf was more effective than *Candida oleophila* in preventing natural infection of nectarines with *Alternaria* spp., *Monilinia fructicola, R. Stolonifer, B. cinerea*, and *P. expansum*.

Example 20

Figure 20:
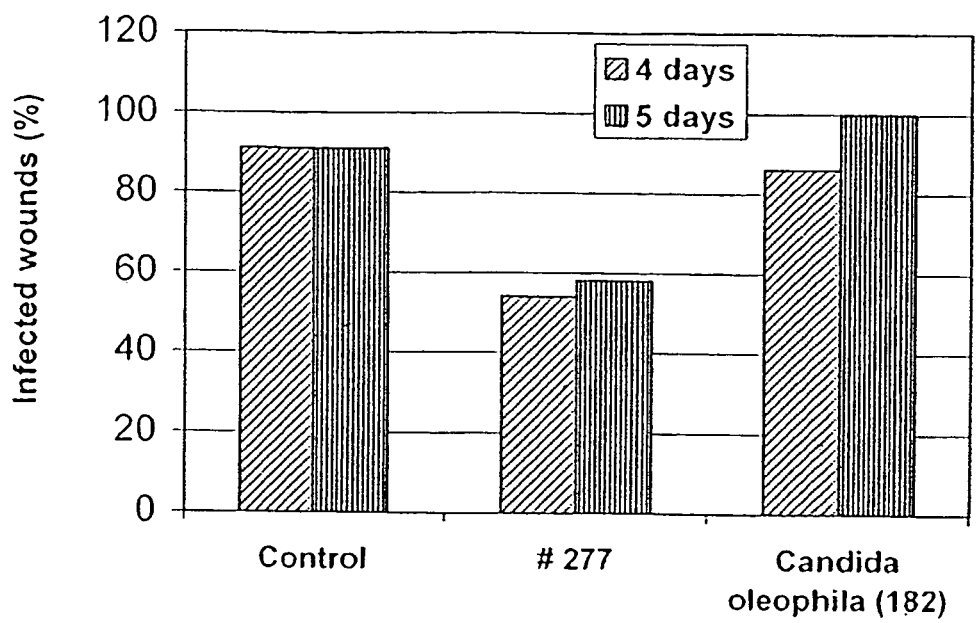
FIG. 20 is a histogram illustrating % infected wounds after artificial infection of nectarines with *Penicillium expansum* in the presence of *Metschnikowia fructicola* (Mf) of the present invention or *Candida oleophila*.

*Metschnikowia fructicola* Inhibits *Penicillium* Infection of Stone Fruit Wounds Stone fruit ('Flavortop' nectarines and 'Swelling' peaches) was wounded with a dissecting needle (1–2 mm deep) and 30 µl of the yeasts-cell suspensions ($10^8$ cells $ml^{-1}$) were applied into each wound. The yeast antagonists used were either *C. oleophila* or *Metschnikowia fructicola* (Mf). Treated fruit was allowed to air dry and then inoculated with 20 µl of *Penicillium expansum* spore suspension ($10^5$ spores.$ml^{-1}$) and kept in plastic trays at 24° C. under humid conditions. The percentage of infected wounds was determined 4 and 5 days after inoculation. Results summarized in FIG. 20 indicate that *Metschnikowia fructicola* (Mf) was more effective than *Candida oleophila* in preventing wound colonization by *Penicillium expansum*.

Example 21

Figure 21:
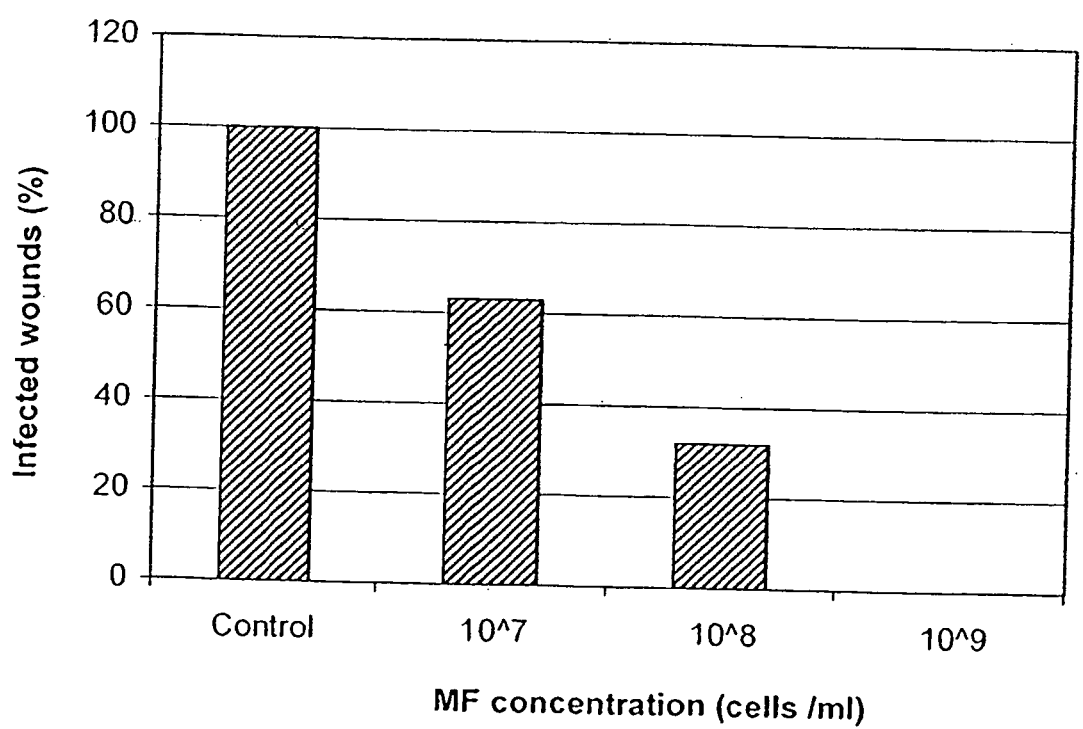
FIG. 21 is a histogram illustrating that the percentage of infected wounds from artificial infection of nectarines with *Penicillium expansum* decreases proportionally to the applied dose of *Metschnikowia fructicola* (Mf) of the present invention.

*Metschnikowia fructicola* Inhibition of *Penicillium* Infection of Stone Fruit is Concentration Dependent Stone fruit ('Flavortop' nectarines and 'Swelling' peaches) were wounded as described in example 20 and 30 µl of varying Mf suspensions ($10^7$, $10^8$ and $10^9$ cells/ml) were applied into each wound. Treated fruit were handled as in example 20 hereinabove. Results, summarized in FIG. 21, indicate that $10^9$ cells/ml of Mf was completely effective in competitively inhibiting wound colonization by *Penicillium expansum* while lower concentrations provided significant degrees of protection.

Example 22

*Metschnikowia fructicola* Inhibits *Penicillium* Infection of Pome Fruit

Golden delicious apples were wounded with a dissecting needle (1–2 mm deep) and 30 ul of varying Mf yeast-cell suspensions ($10^8$ and $10^9$ cells.$l^{-1}$) were applied into each wound. Treated fruits were allowed to air dry and were then inoculated with 20 µl of *Penicillium expansum* spore suspension ($10^5$ spores.$ml^{-1}$) and stored as in examples 20 and 21 hereinabove. The percentage of infected wounds was determined at 5 days after inoculation.

Figure 22:
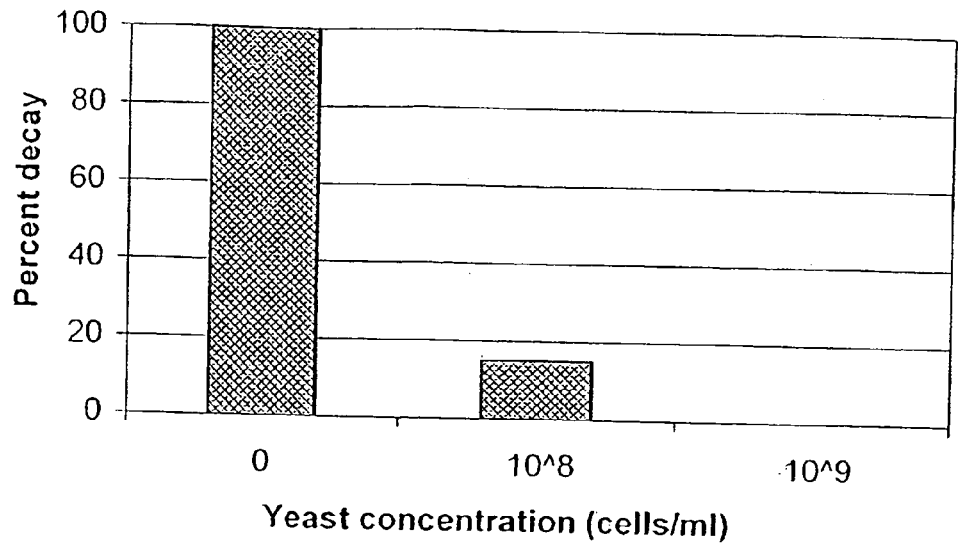
FIG. 22 is a histogram illustrating that total percent decay of apples after artificial infection with *Penicillium expansum* varies with the applied concentration of *Metschnikowia fructicola* (Mf) of the present invention.

Results summarized in FIG. 22 indicate that in pome fruit, as in stone fruit, $10^9$ cells/ml of Mf was completely effective in competitively inhibiting wound colonization by *Penicillium expansum* and that lower concentrations provided significant degrees of protection.

Example 23

Pre-Harvest Application of *Metschnikowia fructicola* Inhibits *Botrytis* in Strawberry In order to demonstrate the practicality of pre-harvest application of a yeast antagonist, MF cell suspension at a concentration of $10^8$ cells/ml was applied by back sprayer to strawberry plants in a commercial field at weekly intervals.

Figure 23A:
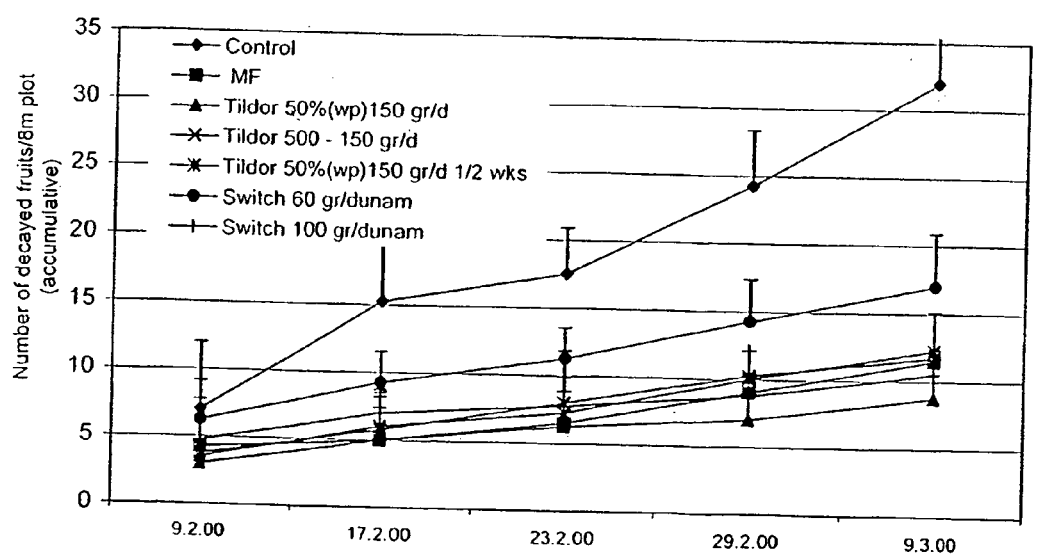
FIGS. 23A and B are a graph and a histogram respectively, illustrating the effect of pre-harvest application of *Metschnikowia fructicola* (Mf) of the present invention on the development of *Botrytis* rot of strawberries in the field (23A) and during post harvest storage (23B). Teldor 50% (WG power formulation)—015%; Teldor 500 (liquid formulation—0.15%; Switch—0.06% (60 g/dunam); Switch 0.1% (100 g/duman).
Figure 23:
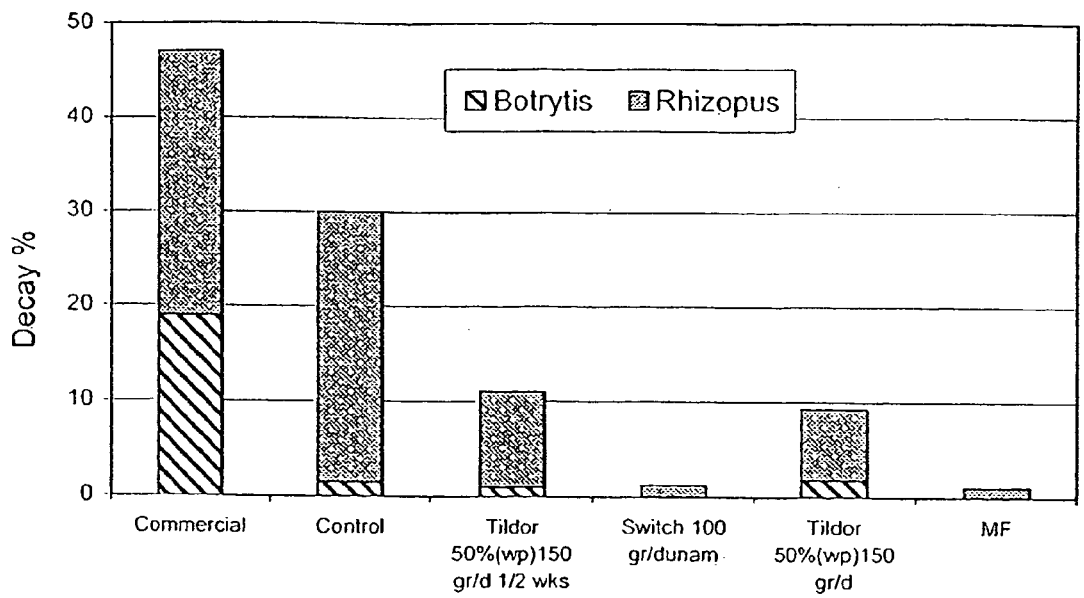

The first application was given at the time of flowering. The yeast treatment was compared with different commercial fungicides at rates indicated in FIG. 23. After the fourth application, the number of decayed fruits in the field was counted in each treatment (FIG. 23A). In addition, fruit were harvested, stored at 1° C. for 3 days followed by 3 days at 24° C. to determine the percentage of decayed fruit (FIG. 23B). These results demonstrate that Mf applied in the field provide protection from rot in the field and during post harvest storage. Mf treatment gave a protection level comparable to that of commercial pesticides.

Example 24

Metschnikowia fructicola Inhibits Green Mold in Grapefruit

In order to demonstrate the versatility of Mf in preventing post harvest decay, green mold decay was determined in grapefruit after 6, 14, 18, 24 days of storage at 20° C. The experiment was done in a pilot scale citrus packing line which simulated commercial operation. At the entering station the fruit received an extensive wash with plain water followed by drying under fans blowing warm air. Fruit were then drenched with an Mf, Metschnikowia raukafii (231) or Candida oleophila (182) cell suspension ($10^8$ cells/ml), dryed under warm air blowers, waxed and packed in commercial cartons. The fruit was kept at 20° C. and checked after different periods of incubation for the presence of decay.

Figure 24:
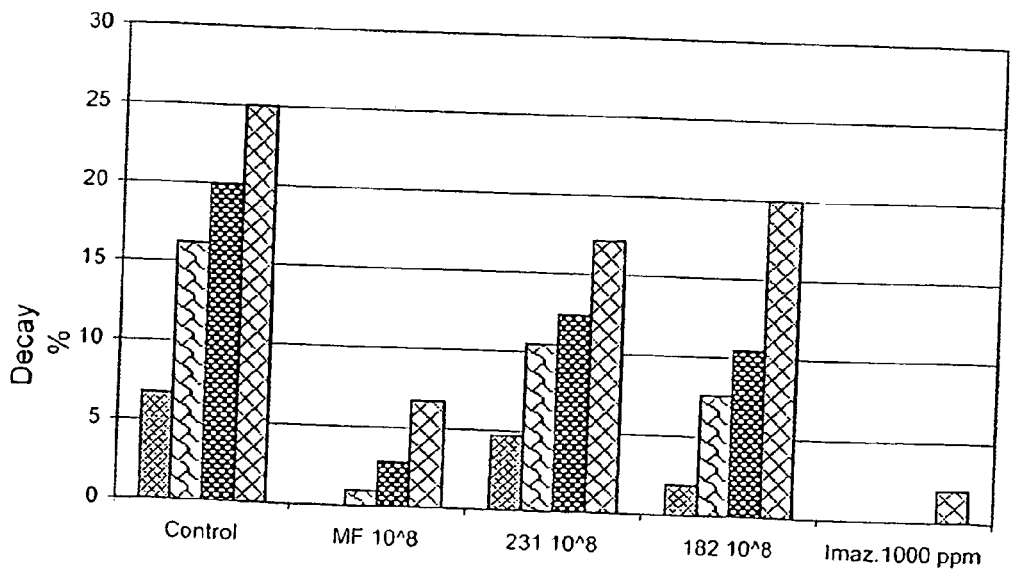
FIG. 24 is a series of histograms illustrating total % decay from green mold decay in grapefruit in the presence or absence of *Metschnikowia fructicola* (Mf) of the present invention or *Metschnikowia raukafii* (231) or *Candida oleophila* (182).

Results summarized in FIG. 24 clearly indicate that Metschnikowia fructicola (Mf) was more effective than Metschnikowia raukafii (231) or Candida oleophila (182) in preventing development of green mold decay in grapefruit.

Example 25

Metschnikowia fructicola Inhibits Botrytis on Tomatoes

Figure 25:
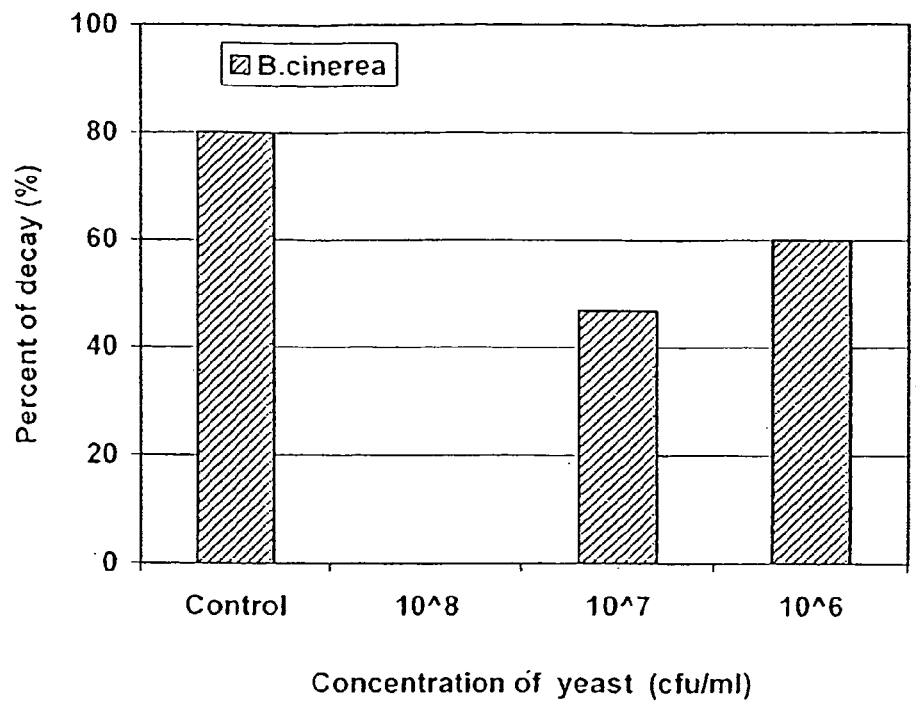
FIG. 25 is a histogram showing concentration dependence of decay % of cherry tomatoes artificially infected with *Botrytis cinerea* to applied *Metschnikowia fructicola* (Mf).

In order to demonstrate the utility of Mf in protecting vegetables, as well as fruits, during storage an assay was conducted on cherry tomatoes. Details of the assay are given in Example 3. Results, summarized in FIG. 25, clearly indicate that concentrations of Mf as low as $10^6$ inhibit development of Botrytis cinerea after artificial infection of cherry tomatoes.

Example 26

Metschnikowia fructicola Inhibits Botrytis on Cherries

In order to examine the relative efficacy of Mf in protecting stone fruit, the ability of C. oleophila and MF to retard development of postharvest decay on sweet cherries was tested. Each yeast antagonist was applied at a concentration of $10^8$ cells/ml. Cherries were dipped for 1 min in various salt solutions or yeast cell suspensions, allowed to air dry and then stored for 30 days at 0° C. followed by 4 days at 24° C. Results, summarized in FIG. 26, clearly indicate Metschnikowia fructicola (Mf) is superior to C. Oleophila in retarding development of natural decay from Botrytis cinerea on sweet cherries both under refrigeration and subsequent storage at room temperature.

Example 27

Figure 27:
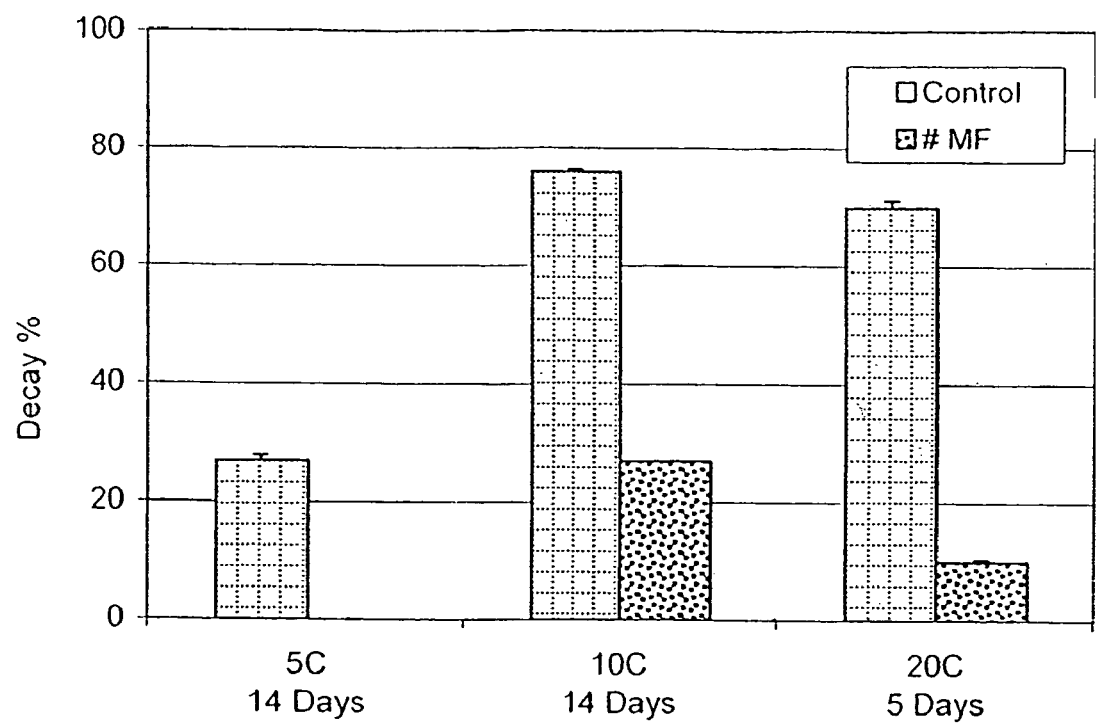
FIG. 27 is a histogram illustrating % decay from *Botrytis cinerea* ($5 \times 10^4$ spores/ml) on cherry tomato in the presence or absence of *Metschnikowia fructicola* (Mf) of the present invention and at different storage temperatures.

Metschnikowia fructicola Inhibits Botrytis on Tomatoes under Various Storage Conditions In order to determine the efficacy of Mf in protecting Cherry tomatoes under various storage conditions, tomatoes were treated with yeast and inoculated with B. cinerea as described hereinabove (Example 3). Tomatoes treated with water and inoculated with B. cinerea served as control. After treatment tomatoes were divided into three groups. One group was incubated at 5° C. for 14 days, the second group was incubated at 10° C. for 14 days and the third group was incubated at 20° C. for 5 days. Results, summarized in FIG. 27, clearly indicate that MF provides significant protection under all conditions tested. Especially impressive is the complete protection afforded tomatoes by Mf under refrigeration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

References

Chalutz, E., and Wilson, C. L., 1990, Postharvest biocontrol of green and blue moldand sour rot of citrus by Debaryomyces hansenii. Plant Dis. 74:134–137.

Droby, S., Chalutz, E., Wilson, C. L., and Wisniewski, M. E., 1989,. Characterization of the biocontrol activity of Debaryomyces hansenii in the control of Penicillium digitatum on grapefruit. Can. J. Microbiol. 35: 794–800.

Droby, S., Wilson, C. L., Wisniewski, M., and El-Ghaouth, A. 2001. Biologically based technology for the control of postharvest diseases of fruits and vegetables. In: Microbial Food Contamination, C. L. Wilson and S. Droby (eds.). CRC Press, Boca Raton, Fla.

Gullino, M. L., Aloi, C., Palitto, M., Benzi, D., and Garibaldi, A., 1991, Attempts atbiocontrol of postharvest diseases of apple. Med. Fac: Landbouw. Rijksuiv. Gent, 56: 195.

Janisiewicz, W. and Roitman, J., 1988, Biological control of blue mold and gray mold on apple and pear with Pseudomonas cepacia. Phytopathol. 78:1697–1700.

Janisiewicz, W. J., Peterson, D. L., and Bors, R., 1994, Control of storage decay of apples with Sporobolomyces roseus. Plant Disease 78:466–470.

Droby, S., Chalutz, E., and Wilson, C. L., 1991, Antagonistic microorganisms as biological control agents of postharvest diseases of fruits and vegetables. Postharvest News and Information 2: 169–173.

Lurie, S., Droby, S., Chalupowicz, L., and Chalutz, E., 1995, Efficacy of Candida oleophila strain 182 in preventing Penicillium expansum infection of nectarine fruits. Phytoparasitica 23:231–234.

Roberts, R. G., 1990, Biological control of mucor rot of pear by *Cryptococcus laurentii, C. flavus*, and *C. albidus*. Phytopathol. 80: 1051.

Chand-Goyal, T., and Spots, R. A. 1996. Control of postharvest pear diseases using natural saprophytic yeast colonists and their combination with low doses of thiabendazole. Postharv. Biol. Technol. 7:51–64.

Ippolito, A., El Ghaouth, A., Wilson, C. L., and Wisniewski, M. 2000. Control of postharvest decay of apple fruit by *Aureobasidium pullulans* and induction of defense responses. Postharv. Biol. Technol. 19:265–272.

El Ghaouth, A., Wilson, C. L., Wisniewski, M. 1998. Ultrastructural and cytochemical aspect of the biocontrol activity of *Candida saitoana* in apple fruit. Phytopathol 88: 282–291.

What is claimed is:

1. A biologically pure culture of a yeast of the species *Metschnikowia fructicola* having all of the identifying characteristics of the deposited sample identified as NRRL Y-30752, said culture capable of competitively inhibiting growth of a deleterious micro-organism on a portion of a plant to which a biologically effective amount of the culture is applied.

2. The yeast of the species *Metschnikowia fructicola* of claim 1, wherein said deleterious micro-organism is selected from the group consisting of *Botrytis cinerea, Aspergillus niger, Penicillium digitatum, Penicillium expansum, Geotrichum candidum, Rhizopus stolonifer, Fusariurn* spp and *Molinilia* spp.

3. The yeast of the species *Metschnikowia fructicola* of claim 1, wherein said plant is selected from the group consisting of a stone fruit, a pome fruit, a citrus fruit, a grape, a berry, a vegetable and an herb.

4. A composition for use in protection of agricultural produce comprising, as an active ingredient, a biologically effective amount of biologically pure yeast *Metschnikowia fructicola* having all of the identifying characteristics of the deposited sample identified as NRRL Y-30752, said composition further containing a carrier.

5. The composition of claim 4, wherein said yeast is supplied in a physiologic state selected from the group consisting of active and dormant.

6. The composition of claim 4, wherein said yeast is supplied in a physical form selected from the group consisting of a liquid suspension, an emulsion, a powder, granules, a lyophylsate and a gel.

7. The composition of claim 4, further comprising a chemical antibiotic.

8. The composition of claim 7, wherein said chemical antibiotic is selected from the group consisting of a fungicide, an antimicrobial agent and a pesticide.

9. The composition of claim 8, wherein said fungicide includes at least one chemical selected from the group consisting of Iprodione, Thiabendazole, Imazalil (1-(2-2,4-Dichlorophenyl)-2(2-propenyloxy-ethyl)-lHimidazol), Fenhexamide, Pyrimethamil and a combination of Fludioxonyl and Cyprodinil.

10. A method of inhibiting growth of a deleterious microorganism on a portion of a plant, the method comprising applying at least one time an agriculturally effective amount of biologically pure culture of yeast *Metschnikowia fructicola* having all of the identifying characteristics of the deposited sample identified as NRRL Y-30752 to the portion of a plant.

11. The method of claim 10, wherein said plant is selected from the group consisting of a pome fruit, a stone fruit, a citrus fruit, a grape variety, a vegetable and a flower bulb.

12. The method of claim 10, wherein said deleterious microorganism is selected from the group consisting of *Botrytis cinerea, Aspergillus niger* and *Rhizopus stolonifer*.

13. An article of manufacture comprising packaging material and a composition for use in protection of agricultural produce from a deleterious micro-organism, comprising, as an active ingredient, a biologically effective amount of biologically pure yeast of the species *Metschnikowia fructicola* having all of the identifying characteristics of the deposited sample identified as NRRL Y-30752, said composition further containing a carrier.

14. The article of manufacture of claim 13, further comprising an applicator designed and constructed to apply said yeast to the agricultural produce.

15. The article of manufacture of claim 13, wherein the agricultural produce is selected from the group consisting of a pome fruit, a stone fruit, a citrus fruit, a grape variety, a flower bulb and a vegetable.

16. The article of manufacture of claim 13, wherein said deleterious micro-organism is selected from the group consisting of *Botrytis cinerea, Aspergillus niger, Penicillium digitatum, Penicillium expansum, Geotrichum candidum* and *Rhizopus stolonifer*.

17. The culture of claim 1, wherein said yeast culture is that deposited as NRRL Y-30752.

* * * * *